(12) United States Patent
Head et al.

(10) Patent No.: US 9,592,201 B2
(45) Date of Patent: *Mar. 14, 2017

(54) GI TRACK DELIVERY SYSTEMS

(75) Inventors: Richard Head, South Australia (AU);
Luz Sanguansri, Hoppens Crossing (AU); Mary Ann Augustin, Victoria (AU)

(73) Assignee: COMMONWEALTH SCIENTIFIC AND INDUSTRIAL RESEARCH ORGANISATION, Campbell (AU)

( * ) Notice: Subject to any disclaimer, the term of this patent is extended or adjusted under 35 U.S.C. 154(b) by 1275 days.

This patent is subject to a terminal disclaimer.

(21) Appl. No.: 10/578,903

(22) PCT Filed: Nov. 22, 2004

(86) PCT No.: PCT/AU2004/001592
§ 371 (c)(1),
(2), (4) Date: Jan. 8, 2007

(87) PCT Pub. No.: WO2005/048998
PCT Pub. Date: Jun. 2, 2005

(65) Prior Publication Data
US 2007/0218125 A1 Sep. 20, 2007

(30) Foreign Application Priority Data
Nov. 21, 2003 (AU) ................ 2003906417

(51) Int. Cl.
*A61K 9/48* (2006.01)
*A61K 9/16* (2006.01)
(Continued)

(52) U.S. Cl.
CPC .............. *A61K 9/1623* (2013.01); *A23D 9/05* (2013.01); *A23L 33/115* (2016.08); *A61K 9/5036* (2013.01); *A23V 2002/00* (2013.01)

(58) Field of Classification Search
CPC ...... A61K 9/1623; A61K 9/5036; A23D 9/05; A23L 33/115; A23V 2002/00
See application file for complete search history.

(56) References Cited

U.S. PATENT DOCUMENTS 4,230,687 A * 10/1980 Sair et al. ................. 424/485
4,755,397 A * 7/1988 Eden ................... A61K 9/1652
106/162.81

(Continued)

FOREIGN PATENT DOCUMENTS

JP  06-141820  5/1994
JP  10-195105  7/1998

(Continued)

OTHER PUBLICATIONS

Kagami et al., Journal of Food Science, vol. 68, No. 7, 2003, 2248-2255.*

(Continued)

*Primary Examiner* — Ernst V Arnold
*Assistant Examiner* — Hong Yu
(74) *Attorney, Agent, or Firm* — Foley & Lardner LLP

(57) ABSTRACT

A micro encapsulation material for use with storage unstable, therapeutic and nutritional agents which release the therapeutic and nutritional agents in predetermined locations in the gastro intestinal tract in which the microencapsulation material is formed by combining a food grade treated carbohydrate with a water soluble food grade protein. The therapeutic and nutritional agents form an oil phase which is emulsified with the water dispersed or dissolved encapsulant to encapsulate the therapeutic and nutritional agents. These agents may be oils or oil soluble or oil dispersible. The agents that may be encapsulated include lipids (oils including oxygen sensitive oils, fatty acids, triglycerides) and oil soluble and oil dispersible ingredients (including pharmaceuticals, probiotics, protein therapeutics (Continued)

and bioactives). The protein used may include any film forming water soluble protein or hydrolyzed protein and includes milk proteins such as casein and its derivatives or whey proteins. The carbohydrate component may be those containing reducing sugar groups, oligosaccharides and starches (raw, modified, resistant, acetylated, proprionylated and butylated starches).

11 Claims, 20 Drawing Sheets

(51) Int. Cl.
    *A23D 9/05* (2006.01)
    *A61K 9/50* (2006.01)

(56) References Cited

U.S. PATENT DOCUMENTS

| | | | |
|---|---|---|---|
| 4,844,919 A | | 7/1989 | Szwerc |
| 4,999,205 A | * | 3/1991 | Todd, Jr. .................. 426/250 |
| 5,108,758 A | | 4/1992 | Allwood et al. |
| 5,387,426 A | | 2/1995 | Harris et al. |
| 5,436,019 A | | 7/1995 | Harris et al. |
| 5,444,054 A | | 8/1995 | Garleb et al. |
| 5,455,342 A | | 10/1995 | Redding, Jr. |
| 5,498,439 A | * | 3/1996 | Bonner .................... 426/650 |
| 5,547,513 A | | 8/1996 | Mallee et al. |
| 5,840,860 A | | 11/1998 | Annison et al. |
| 5,866,619 A | | 2/1999 | Sintov et al. |
| 5,945,528 A | | 8/1999 | Sommermeyer et al. |
| 5,952,314 A | | 9/1999 | DeMichele et al. |
| 6,048,563 A | | 4/2000 | Swartz et al. |
| 6,234,464 B1 | | 5/2001 | Krumbholz et al. |
| 6,368,629 B1 | | 4/2002 | Watanabe et al. |
| 6,403,130 B2 | | 6/2002 | Beyer |
| 6,413,567 B1 | | 7/2002 | Dudacek et al. |
| 6,531,152 B1 | | 3/2003 | Lerner et al. |
| 6,613,373 B2 | | 9/2003 | Haynes et al. |
| 6,689,389 B2 | | 2/2004 | Gustavsson et al. |
| 6,737,099 B2 | | 5/2004 | Guraya |
| 8,871,266 B2 | * | 10/2014 | Crittenden .............. A61K 9/19 424/484 |
| 2003/0026888 A1 | | 2/2003 | Guraya |
| 2003/0152629 A1 | * | 8/2003 | Shefer et al. .................. 424/484 |
| 2003/0185960 A1 | * | 10/2003 | Augustin ............... A23D 7/003 426/602 |
| 2005/0287276 A1 | * | 12/2005 | Lavoie ..................... A23L 2/40 426/590 |
| 2006/0008575 A1 | | 1/2006 | Armbrecht et al. |
| 2006/0159825 A1 | | 7/2006 | Smith et al. |
| 2007/0122397 A1 | * | 5/2007 | Sanguansri et al. ....... 424/93.45 |
| 2007/0212475 A1 | | 9/2007 | Augustin et al. |

FOREIGN PATENT DOCUMENTS

| | | |
|---|---|---|
| JP | 10-324642 | 12/1998 |
| WO | WO 01/74175 A | 10/2001 |

OTHER PUBLICATIONS

Wheat Flour [online], retrieved from internet: http://en.wikipedia.org/wiki/Flour. [Retrieved on Feb. 7, 2011].*
Hylon VII: retrieved from internet: http://eu.foodinnovation.com/docs/HYLONVII.pdf. Retrieved on May 13, 2013.*
Dispersion: retrieved from inernet: http://en.wikipedia.org/wiki/Dispersion_(chemistry). Retrieved on Dec. 5, 2013.*
Paste: retrieved from internet: (http://www.thefreedictionary.com/paste. Retrieved on Dec. 5, 2013.*
Reducing sugar: retrieved from internet: http://en.wikipedia.org/wiki/Reducing_sugar. Retrieved on Dec. 5, 2013.*
100 years of food starch technology: retrieved from internet: asia.foodinnovation.com/pdfs/100years.pdf. Retrieved on Dec. 5, 2013.*
Capsul: retrieved from internet: sp.ingredion.us/_layouts/ns_prod/DBDocuments.aspx?DocumentId . . . Retrieved on Dec. 5, 2013.*
Zhang et al.: Preparation of resistant starch by hydrolysis of maize starch with pullulanase, Carbohydrate Polymers, 83, 2011, 865-867.*
Emulsion dispersion: retrieved from internet; http://en.wikipedia.org/wiki/Emulsion_dispersion. Retrieved on Dec. 5, 2013.*
Caseinate: retrieved form internet: http://www.merriam-webster.com/dictionary/caseinate. Retrieved on Dec. 5, 2013.*
Encapsulate: retrieved from internet: http://www.merriam-webster.com/dictionary/encapsulate. Retrieved on Dec. 1, 2014.*
Sajilata et al.: Comprehensive Review in Food Science and Food Safety, Institute of Food Technologists, 2006, vol. 5, issue 1, p. 1-17.*
Bai et al.: Structural Changes from Native Waxy Maize Starch Granules to Cold-Water-Soluble Pyrodextrin during Thermal Treatment, Journal of Agriculture and Food Chemistry, 2014, 62, 4186-4194.*
Human gastrointestinal tract: retrieved from internet: https://en.wikipedia.org/wiki/Human_gastrointestinal_tract.*
Shogren et al.:Distribution of Octenyl Succinate Groups in Octenyl Succinate Anhydride Modified Waxy Maize Starch, Starch, 52, 2000, 196-204.*
Chiu et al.: Modification of Starches (Starch: Chemistry and Technology, 3rd Edition, 2009, Elsevier Inc.*
T. Kagarni et al., "Oxidative Stability, Structure and Physical Characteristics of Microcapsules Formed by Spray Drying of the Fish Oil with Protein and Dextrin Wall Materials", Journal of Food Science, vol. 68, No. 7, 2003, pp. 2248-2255.
Augustin et al, "Microencapsulation of food ingredients", Food Australia, 2001, 53, pp. 220-223 (4 pgs).
Brazel, C.S., "Microencapsulation: offering solutions for the food industry", Cereal Foods World, 1999, 44(6), pp. 388-393 (5 pgs).
Chung et al., "Physiochemical properties of sonicated mung bean, potato and rice starches", Cereal Chemistry, 2002, 79(5), pp. 631-633 (3 pgs).
Dommels et al., "Dietary n-6 and n-3 polyunsaturated fatty acids and colorectal carcinogenesis: results from cultured colon cells, animal models and human studies", Environmental Toxicology and Pharmacology, 2002, vol. 12 (4), 233-244 (12 pgs).
Douzals et al., "High pressure gelatinization of wheat starch and properties of pressure-induced gels", J. Agric. Food Chem., 1998, 46, pp. 4824-4829, (6 pgs).
Isono et al., "Ultrasonic degradation of waxy rice starch", Biosci. Biotech. Biochem, 1994, 58(10), pp. 1799-1802(4 pgs).
Karmali, Radasha A., Historical Perspective and Potential Use of n-3 Fatty Acids in Therapy of Cancer Cachexia, Nutrition, 1996, vol. 12 (1), S2-S4 (3 pgs).
Onwulata et al., "Starches and fibers treated by dynamic pulsed pressure", Food Research International, 2000, 33, pp. 367-374 (8 pgs).
RSTAR 11/02, AOAC Method 2002.03; AACC Method 32-40, Megazyme, pp. 1-15 (16 pgs).
Rubinstein et al., "The rationale for peptide drug delivery to the colon and the potential for polymeric carriers as effective tools" J. Controlled Release, 1997, 46, pp. 59-73 (15 pgs).
Rubinstein, Abraham, "Natural Polysaccharides as targeting tools of drugs to the human colon", Drug Development Research, 2000, 50, pp. 435-439 (5 pgs).
Seguchi et al., "Study of wheat starch structures by sonication treatment", Cereal Chemistry, 1994, 71 (6) pp. 636-639(4 pgs).
Sinha et al., "Microbially triggered drug delivery to the colon", Eur. J. Pharmaceutical Sciences, 2003, 18, pp. 3-18 (16 pgs).
Sinha et al., "Polysaccharides in colon-specific drug delivery", Int. J. Pharmaceutics, 2001, 224, pp. 19-38 (20 pgs).
Stolt et al., "Evaluation and modeling of rheological properties of high pressure treated waxy maize starch dispersions", Journal of Food Engineering, 1999, 40, pp. 293-298 (6 pgs).
Vandaamme et al., "The use of polysaccharides to target drugs to the colon", Carbohydrate Polymers, 2002, 48, pp. 219-231 (13 pgs).
US Office Action on Mar. 3, 2010.
US Office Action on Aug. 11, 2010.

(56) References Cited

OTHER PUBLICATIONS

Non-Final Office Action U.S. Appl. No. 11/587,566 dated Feb. 17, 2011.
Office action dated Jul. 31, 2014 issued in U.S. Appl. No. 11/587,566.
Final Office Action dated Feb. 26, 2015 in U.S. Appl. No. 11/587,566 (10 pages).

* cited by examiner

Fig. 16.

GI TRACK DELIVERY SYSTEMS

This invention relates to microencapsulated formulations for delivery of nutritional and pharmaceutical agents to the gastro intestinal tract and in particular the colon. The compositions may be used for protection and delivery of nutrients or nutraceuticals in processed foods.

BACKGROUND TO THE INVENTION

Microencapsulation involves the packaging of small particles of solid, liquid or gas within a secondary material to form a microcapsule. It has been used for targeted delivery of drugs in the body in the pharmaceutical industry. It is increasingly being seen as a technology that offers novel food processing solutions. With the use of microencapsulation, possible undesirable interactions between the added nutraceutical and other components in the food or its environment can be avoided and the site of release of the added component can be manipulated. The appropriate application of microencapsulation technology enables the fortification of food without affecting the taste, aroma or texture of food. It can afford protection to sensitive food ingredients and enhance the shelf-life and stability of fortified foods (Brazel, C. S. (1999) Microencapsulation: offering solutions for the food industry. *Cereal Foods World* 44(6): 388-393; Augustin, M. A., Sanguansri, L., Margetts, C. and Young. B. (2001) Microencapsulation of food ingredients. *Food Australia* 53 220-223).

Microencapsulation can serve both the purposes of the food and health industries, as it is a key technology with potential for the delivery of dietary bioactives and development of successful marketable functional foods. Addressing this challenge, requires tailoring the performance of food grade microcapsules in a food processing environment so that essential sensitive components are protected during food manufacture and the microcapsules can also meet the need for site specific delivery within the gastrointestinal tract.

Directing nutraceuticals and therapeutics of the colon is of interest for treatment of colon diseases (Rubinstein, A., Tirosh, B., Baluom, M., Nassar, T., David, A., Radai, R., Gliko-Kabir, I. And Friedman, M. (1997). The rationale for peptide drug delivery to the colon and the potential for polymeric carriers as effective tools. *J. Controlled Release* 46, 59-73). Targeting to colon has been carried out by formation of pro-drugs which are enzymatically cleaved in the colon, and multi-coats with pH sensitive and pressure dependent release. Often enteric acrylic polymers are used to protect cores in colon-delivery formulations. Biopolymers, particularly polysaccharides, may be used for targeting cores to the colon where the release of cores is triggered by the microflora in the colon. A range of polysaccharides such as chitosan, pectin, arabinoxylan, arabinogalactan, xylan, cellulose dextrans, guar gum, amylose, inulin and mixtures of these have been examined and shown to have potential as colon-delivery systems (Rubinstein, A. (2000) Natural Polysaccharides as targeting tools of drugs to the human colon. *Drug Development Research* 50, 435-439; Sinha, V. R. and Kumaria, R. (2001) Polysaccharides in colon-specific drug delivery *Int. J. Pharmceutics* 224, 19-38; Vandaamme, Th. F., Lenourry, A., Charrueau, C. and Chaumeil, J.-C. (2002) The use of polysaccharides to target drugs to the colon. *Carbohydrate Polymers* 48, 219-231; Sinha, V. R. and Kumaria. R. (2003) Microbially triggered drug delivery to the colon. *Eur. J. Pharmaceutical Sciences* 18, 3-18).

There have been a number of attempts to use biopolymers for colon delivery and for treating colonic diseases U.S. Pat. No. 5,952,314 discloses an enteral product comprising an oil blend with fatty acids {EPA (C20:5) and DHA (C22:6)} and a source of indigestible carbohydrate which is metabolised to short chain fatty acids in the colon. It has use for improving nutritional status and treating ulcerative colitis U.S. Pat. No. 5,108,758 discloses a glassy amylose matrix for delivery of medication to the colon U.S. Pat. No. 5,840,860 is concerned with delivery of short chain fatty acids (SCFA) to the colon by way of a modified starch.

Japanese patent 10324642 discloses a colon delivery system for delivery of bioactives (eg peptides) comprising inner layer of chitosan and outer-layer of gastric resistant material such as wheat gliadin or zein.

U.S. Pat. No. 5,866,619 discloses a colonic delivery system for drugs such as proteins and peptides comprising a saccharide containing polymer U.S. Pat. No. 6,368,629 discloses a drug coated with an organic acid-soluble polymer and a saccharide for colon delivery.

U.S. Pat. No. 5,444,054 discloses a method of treating colitis with a composition containing oil blend (with DHA/EPA) and a source of indigestible carbohydrate (CHO) which is metabolised to short chain fatty acids.

U.S. Pat. No. 5,952,314 is concerned with an enteral nutritional product for treatment of colitis which comprises oil containing EPA/DHA and a source of indigestible carbohydrate which is metabolised to short chain fatty acids.

U.S. Pat. No. 6,531,152 describes a drug delivery system containing a water soluble core (Ca pectinate or other water-insoluble polymers) and outer coat which bursts (eg hydrophobic polymer—Eudragrit) for delivery of enterally-administered drugs to specific locations along the gastrointestinal tract There are proposals using combinations of proteins and polysaccharides for the formation of coating systems.

U.S. Pat. No. 6,234,464 discloses a system in which oils/polyunsaturated fatty acids (PUFA)/fatty acids are provided with capsules comprised of two layers in which the inner layer consists of gelatin, casein or alginate and the outer layer consists of gelatin, gum arabic, chitosan to provide a product stable in boiling water U.S. Pat. No. 6,403,130 discloses a coating composition comprising a polymer containing casein and high methoxy pectin (amide formed by reaction of ester group R'COOCH$_3$ of pectin with free amino group of protein R"NH$_2$)

WO 01/74175 discloses the encapsulation of oxygen sensitive materials such as polyunsaturated oils in a protein carbohydrate film treated to form a Maillard reaction product.

It is an object of this invention to provide a gastrointestinal delivery system that can be used with storage unstable ingredients as well as providing protection during delivery through the gut.

BRIEF DESCRIPTION OF THE INVENTION

To this end the present invention provides a micro encapsulation material for use with storage unstable, therapeutic and nutritional agents which release the therapeutic and nutritional agents in predetermined locations in the gastro intestinal tract in which the microencapsulation material is formed by combining a food grade treated carbohydrate with a water soluble food grade protein.

The therapeutic and nutritional agents form an oil phase which is emulsified with the water dispersed or dissolved encapsulant to encapsulate the therapeutic and nutritional agents. These agents may be oils or oil soluble or oil dispersible which in the latter case may include water soluble ingredients.

The agents that may be encapsulated include lipids (oils including oxygen sensitive oils, fatty acids, triglycerides) and oil soluble and oil dispersible ingredients (including pharmaceuticals, probiotics, and bioactives). Water dispersible components including those that partition between oil and water phases may also be encapsulated. When water dispersible therapeutic and nutritional agents are used they may not be encapsulated with the oil phase but may be dispersed in the encapsulant film. The emulsions may be used as food ingredients or therapeutic agents but preferably the emulsions are dried to form powders.

Prior art encapsulation systems did not consider the use of combinations of proteins with other biopolymers for formation of capsules for target delivery of sensitive cores to the colon.

The delivery systems of this invention enable pharmaceutical and food manufacturers to offer a range of nutritionally and physiologically functional food ingredients and bioactive compounds in convenient formats and using all natural ingredients which will also enable the delivery of these products to the colon. Some of the encapsulants used for colon delivery in this invention have the added benefits of being effective matrices for encapsulating oxygen sensitive ingredients. The film-forming and anti-oxidant properties of some of the encapsulants used work synergistically to preserve sensitive ingredients such as polyunsaturated fatty acids from being oxidised during storage and also protects them during exposure to high temperature, pressure and moisture encountered during the processing of foods. In addition, this invention uses readily available proteins and carbohydrates. There are no solvents used in the preparation of the encapsulated formulations as the process is an all-aqueous based system. The processes can be easily incorporated or adapted to suit most food and pharmaceutical manufacturing plants with drying operations.

The protein used may include any film forming water soluble protein or hydrolysed protein and includes milk proteins such as casein and its derivatives or whey proteins. The carbohydrate component may be those containing reducing sugar groups, oligosaccharides and starches (raw, modified, resistant, acetylated, proprionated and butylated starches).

The proteins and carbohydrates may be reacted in aqueous solutions to obtain conjugates. The reaction, which occurs, can be between free amine groups of amino acids in the protein and reducing sugar groups in the carbohydrate. This type of reaction is generally termed a Maillard reaction typically occurring in the non-enzymatic browning of foods. This reaction occurs during heat processing of foods and has previously been shown to be beneficial for engineering desirable encapsulating properties for protection of oxygen sensitive components. For example, microencapsulated formulations containing oxygen sensitive oils are protected against oxidation as the Maillard reaction products [MRP] in the encapsulating matrix are good film-formers and also exhibit anti-oxidation activity as disclosed in WO 01/74175.

The starches used in the formulations may also be pre-processed using conventional and emerging processing technologies to modify the starch properties to provide improved processing characteristics during the preparation of the delivery systems. The pretreatments are chosen to break down the long starch molecules so that they form more stable emulsions and also to provide a larger number of terminal sugar reducing groups for Maillard reaction with the protein component of the encapsulant.

Colon delivery systems may be used for range of bioactives (e.g. oils), pharmaceuticals and therapeutics, which are unstable in the upper gastrointestinal tract. The protection afforded to the encapsulated components by the encapsulating material enable target release in the colon where the release is achieved after the encapsulant is degraded (e.g. by the action of microbial enzymes in the colon). Delivery of bioactives, pharmaceuticals and therapeutic components to the colon is desirable for treatment and prevention of diseases of the colon such as colorectal cancer, ulcerative colitis and inflammatory bowel disorder.

In some cases the encapsulants used in the formulations such as selected polysaccharides, can also serve as gut wall adherents or as prebiotics that facilitate growth of beneficial bacteria, and can offer added advantages. For example delivery systems containing resistant starch have potential benefits on colonic health.

BRIEF DESCRIPTION OF DRAWINGS

FIGS. 19A and 19B show the result of the in-vivo experiments conducted to assess release characteristics of formulation discussed in example 19.

DETAILED DESCRIPTION OF THE INVENTION

Figure 1:
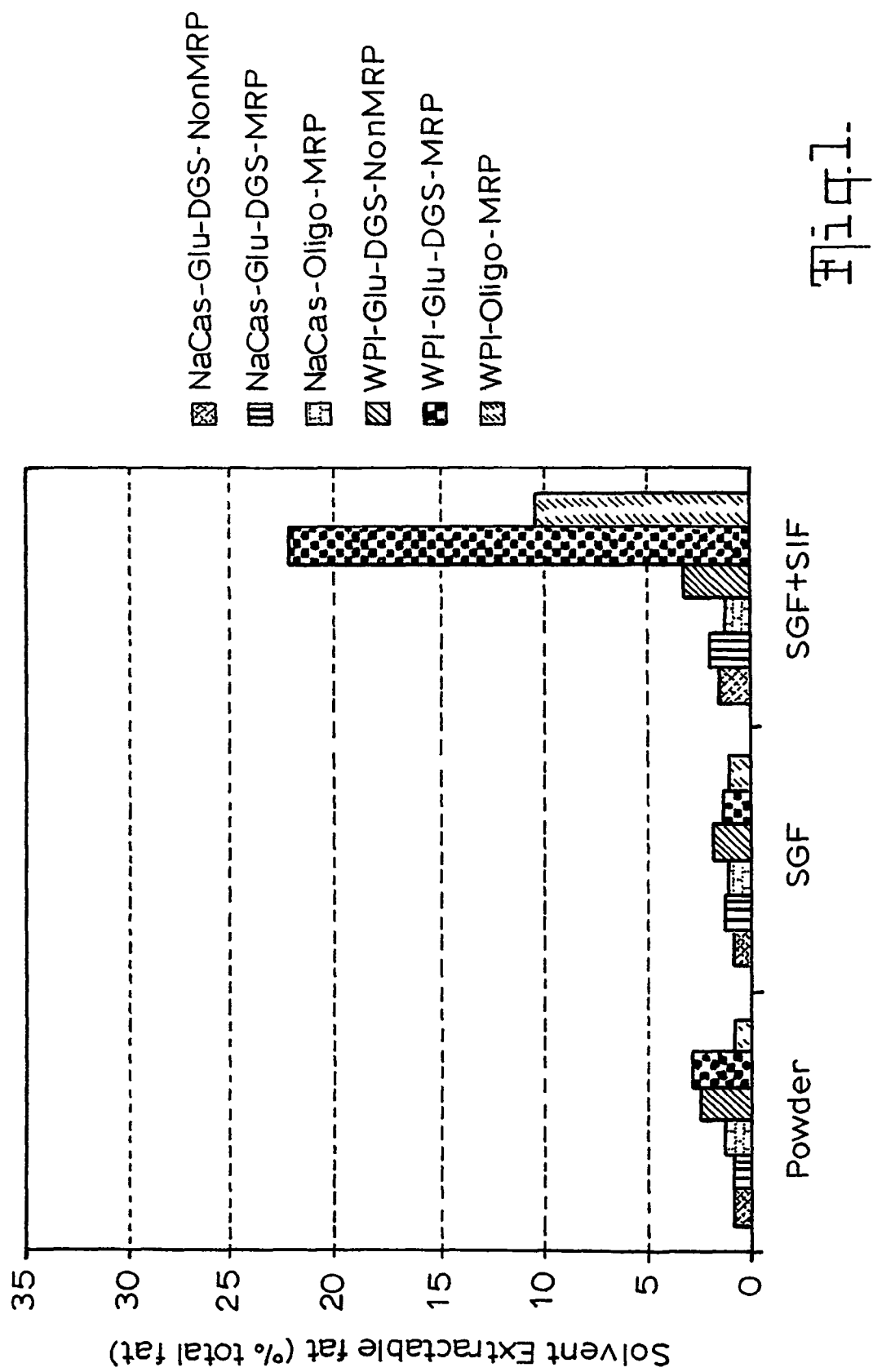
FIG. 1 shows the properties related to solvent extractable fat associated with formulations discussed in example 1.

A number of formulations will be described, some according to the invention and some for comparative purposes to show that some formulations are suitable to delivery to the colon whilst others could be more suitable for release in the small intestine. These formulations demonstrate that the core is protected from digestion in the stomach and the environment in the small intestine.

FIGS. 1 to 19 of the drawings graphically illustrate the solvent extractable fat content and other properties of the formulations of the invention as illustrated in examples 1 to 19 below.

The process of microencapsulating the active component involves the following manufacturing steps:
 (a) Selection of the biologically active core (e.g. oil, oil soluble or oil dispersible material, bioactives, therapeutics, pharmaceuticals)
 (b) Dispersion of the protein and carbohydrates (or starch that has been pre-processed by conventional means such as heating or extrusion or by the use of emerging processing technologies such as high pressure processing, microfluidisation or ultrasonics) in the aqueous phase and treatment of the mixture. If desired, the protein-carbohydrate blends may be further heat processed to induce the formation of conjugates (e.g. Maillard reaction products)
 (c) Mixing the core with the encapsulant (i.e. protein-carbohydrate mixture) and homogenizing the mixture to obtain an emulsion, in which the core is surrounded by the encapsulant.
 (d) Optionally, spray drying the emulsion to obtain a powdered formulation in which the core is surrounded by the encapsulating matrix Emulsion Formulations Tuna fish oil was used as an oil of choice in most of these examples since it contains a high amount of long chain polyunsaturated fatty acids and this need to be protected from oxidation prior to consumption. In addition there is interest in delivering these to the colon because of their potential for prevention of colorectal cancer and promotion of bowel health (Karmeli, R A. (1996) Historical Perspective and Potential Use of n-3 Fatty Acids in Therapy of Cancer Cachia. *Nutrition*, Vol 12 (1) S2-S4; Dommels Y E M, Alink, G M, van Bladeren, P J, van Ommen, B (2002) Dietary n-6 and n-3 polyunsaturated fatty acids and colorectal carcinogenesis: results from cultured colon cells, animal models and human studies, Environmental *Toxicology and Pharmacology*, Vol 12 (4), 233-244). Tributyrin and lutein were also included as examples. The encapsulation of probiotics (i.e. an example of a water dispersible component) using this technology has been previously disclosed in WO 01/74175.

A range of formulations was prepared using protein and/or carbohydrate (raw or pre-processed) and oil mixtures at different ratios. The formulations were made-up to contain 25 and 50% fat in the final powder.

The protein used in these examples were sodium caseinate, whey protein isolate and hydrolysed milk proteins. The carbohydrates used, alone or in combination, were glucose, oligosaccharides, dried glucose syrup, modified starches, resistant starches and native starches. Polysaccharides, including high-methoxy pectin, alginate, carrageenan, guar gum, were added to protein-carbohydrate mixtures in some formulations.

Manufacture of Microcapsules

Materials

The core materials used in the examples include: tuna oil, tributyrin and 15% (w/w) lutein (mostly as dipalmitate and dimyristate lutein esters) in soy bean oil.

Proteins used as encapsulant in the examples include: sodium caseinate (NaCas), whey protein isolate (WPI), hydrolysed casein protein (HCP) and hydrolysed whey protein (HWP).

Carbohydrates used in the examples include: dextrose monohydrate (Glu), waxy maize, maize starch, dried glucose syrup (DGS), wheat starch, oligofructose (oligo), tapioca dextrin (K4484), modified starch (Capsul), modified starch (Hi-Cap 100), Hi-Maize, Hylon VII, Novelose 260 and Novelose 330, potato starch, sodium alginate, kappa carrageenan, high methoxy pectin (HMP) and guar gum.

Preparation of Protein-Carbohydrate Encapsulants

In some cases, unreacted blends of protein and carbohydrates (referred to as NonMRP formulations since these were not heated to induce the formation of Maillard reaction products) were used as the encapsulating matrix. For the preparation of reacted protein-carbohydrate encapsulants (referred to as MRP formulations as these were heated to induce the formation of Maillard reaction products), protein was dissolved in 60° C. water, using a high shear mixer, and then the sugars, starch or the selected carbohydrate were added. Where a polysaccharide was also added, the polysaccharide was first allowed to hydrate in water at 90° C. temperature before addition into the protein-sugar mixture. The pH of the protein-sugar/starch/gum mixtures was adjusted to 7.5. The mixture were then filled into 3 liter cans, sealed and heated in the retort to 98° C. and held for 30 minutes, then cooled down to room temperature. Microcapsule formulations are given in the examples below together with the methods used for the manufacture of microcapsules.

Preparation of Protein-Starch Encapsulants

Protein was dissolved in 60° C. water to make 15% total solids (TS) solution, using a high shear mixer. Starch (raw or heated, heated and microfluidised, extruded, high pressure processed and ultrasonicated) was prepared and processed separately to make a 10% TS solutions or dispersions in 70° C. water (See Preparation of Starches for Microencapsulation detailed below). The 15% TS protein solution were mixed together with the 10% TS starch to get a 12% TS mixture with a 1:1 protein:starch ratio. Where MRP was required, the mixture were then filled into 3 liter cans, sealed and heated in the retort to 98° C. and held for 30 minutes, then cooled down to 60° C.

Preparation of Starches for Microencapsulation

Raw or Unprocessed

10% TS starch dispersion (no pre-treatment applied) was mixed with 15% TS of protein solution at 60° C.

Heat Processing

20% TS of each starch dispersion (except for potato starch where a 10% TS dispersion was used due to high viscosity at 20% TS) were heated at 121° C. for 60 minutes in a 73×82 mm cans. Once heat processed, 70° C. deionised water was added to dilute the sample to 10% TS in a high shear mixer. This heat processed starch was mixed with 15% TS of protein solution at 60° C. This mixture was then used for microencapsulation of bioactives.

Heat Processing and Microfluidisation Treatment

20% TS of each starch dispersion (except for potato starch where a 10% TS dispersion was used due to high viscosity at 20% TS) were heated at 121° C. for 60 minutes in a 73×82 mm cans. Once heat processed, 70° C. deionised water was added to dilute the sample to 10% TS in a high shear mixer, and processed at 60° C. through a pilot scale M-210B EH microfluidiser (MFIC, Newton Mass., USA). The plant was operated at 800 bars and 3 passes using a combination of 425 µm Q50Z auxiliary processing module and 200 µm E230Z interaction chamber (for dispersion and cell disruption). The microfluidised (MF) starch was mixed with 15% TS of protein solution at 60° C. for microencapsulation.

Heat Processing and Ultra-High Pressure Treatment

20% TS of a starch dispersion was heated at 121° C. for 60 minutes in a 73×82 mm cans. Once heat processed, 70° C. deionised water was added to dilute the sample to 10% TS in a high shear mixer, and processed by ultra-high pressure treatment at 6,000 bars for 15 minutes using HPP-QFP 35 L unit. The ultra-high pressure treated (HPP) starch was mixed with 15% TS of protein solution at 60° C. for microencapsulation.

Heat Processing and Ultrasonics Treatment

20% TS of a starch dispersion was heated at 121° C. for 60 minutes in 73×82 mm cans. Once heat processed, 70° C. deionised water was added to dilute the sample to 10% in a high shear mixer, and processed with ultrasound treatment at 50 ml/min @ 380 watts using 20 KHz unit. The ultrasound treated (US) starch was mixed with 15% TS of protein solution at 60° C. for microencapsulation.

Extrusion

Resistant starches were processed using a twin-screw extruder (model MPF 40, APV Baker, Peterborough PE3-6TA, England) 40 mm screw diameter and length to diameter ratio of 25:1, and a low shear screw configuration. A 4 mm die was used throughout the trial. Raw materials were fed into feed port 1 at 15 kg h$^{-1}$ for resistant starch processing using a gravimetric feeder (Ktron Soder AG CH-5702, Niederlenz) and water was injected into port 2 with a volumetric pump (Brook Crompton, Huddersfield, England). Barrel moisture was injected at 20-40% and the die melt temperature was varied from 140 to 178° C. with increasing screw speed from 150-250 rpm. The extruded resistant starches were milled to 0.2 mm particle size powder. 10% TS extruded starch dispersion was mixed with 15% TS of protein solution at 60° C. for microencapsulation.

Preparation of Oil in Water Emulsions

The protein-carbohydrate mixtures and the tuna oil were pre-heated to 60° C. separately. The bioactive core was added into the protein-carbohydrate mixture using a Silverson high shear mixer. The mixture were then homogenised at 350 and 100 bar pressures in two stages using a Rannie homogeniser.

Spray Drying of Emulsions

The homogenised emulsions were spray dried at 50-60° C. feed temperature, 180° C. inlet temperature and 80° C. outlet temperature using a Niro production minor spray dryer. The powder was collected from the main chamber and packed.

Estimation of Solvent Extractable Fat in Tuna Oil Powders

The estimation of solvent-extractable was based on the method by Pisecky (Handbook of Milk Powder Manufacture, 1997) except that petroleum ether was used in place of carbon tetrachloride. Fifty ml of petroleum ether (b.p. 40-60° C.) was added to 10 g powder. The mixture was agitated in a stoppered flask for 15 minutes. The mixture was filtered and the solvent evaporated at 60° C. using a rotary evaporator. The remaining fat residue was then dried in an oven at 105° C. for 1 h.

In-Vitro Testing of Microcapsules

The stability of the microcapsules in the stomach and the small-intestine was estimated by assessment of oil-release properties of microcapsules (a) incubated in simulated gastric fluid (SGF) (pH 1.2) for 2 h at 37° C. and 100 rpm in a shaker water-bath incubator and (b) incubated in SGF (2 h at 37° C. and 100 rpm in a shaker water-bath incubator) followed by exposure to simulated intestinal fluid (SIF) (pH 6.8) (3 h at 37° C. and 100 rpm). SGF and SIF were prepared according to the methods given in the US Pharmacopoeia (US Pharmacopeia 2000 & National Formulatory (USP 24 NF 19), Rockville, Md.)

For Estimation of Released Oil from Microcapsules In-Vitro:

The solvent extractable fat from the incubated samples were measured. The sample was transferred into a 250 ml stoppered separating funnel and extracted with petroleum ether (75 ml plus 2×25 ml). The sample was filtered through a phase separation filter paper to obtain the solvent phase after each extraction. The solvent was removed to recover the oil released.

For Estimation of Released Lutein In-Vitro:

The microcapsule containing the lutein (1.0 g) was incubated sequentially with SGF (pH 1.2) and SIF (pH6.8) as outlined above. For estimation of released lutein, the solvent extractable lutein from the incubated samples was measured. The extraction was performed in a centrifuge tube. The sample was extracted with petroleum ether (15 ml plus 2×10 ml). The sample was centrifuged (2000 rpm for 10 min) after each extraction and the top solvent layer removed. The combined solvent extracts were filtered through a phase separation filter paper prior to dilution with petroleum ether. The absorbance of the diluted extract was measured at 444 nm and the concentration of extracted lutein was determined.

For Estimation of Released Tributyrin In-Vitro:

The microcapsule containing the tributyrin (1.0 g) was incubated sequentially with SGF (pH 1.2) and SIF (pH 6.8) as outlined above. For estimation of released tributyrin samples that were exposed to SGF only were used directly and that exposed sequentially to SGF and SIF was adjusted to pH 2. To this mixture was added 2.5 g NaCl and 15 ml dichloromethane and the mixture was centrifuged at 2500 rpm for 10 min at 5 C. The aqueous layer was removed and kept while the dichloromethane layer was decanted into a conical flask without disturbing the gelatinous precipitate floating on top of the dichloromethane layer. The aqueous layer with the gelatinous precipitate was extracted with another 15 ml dichloromethane. The dichloromethane extracts were dried over anhydrous $Na_2SO_4$, before filtering (0.45 µm PTFE syringe filter). The dichloromethane was removed under Nitrogen in a warm water bath. The extracted material was dissolved in 10 ml hexane/iso-propyl alcohol (99:1, v/v) and the solution stored in freezer. The amount of tributyrin and butyric acid in the extract was analysed by normal-phase HPLC. [Column: PVA-Sil guard and analytical (250 mm×4.6 mm I.D.) columns; UV detector (210 nm)].

In-Vivo Testing of Microcapsules

Male Sprague-Dawley rats, approximately 10 weeks of age were used for the in-vivo study. Rats were denied solid food for 24 hours prior to dosing, but were allowed free access to drinking water containing 2.5% glucose, 0.5% NaCl and 0.005% KCl (all w/v).

Preparation of Radiolabelled Tuna Oil:

0.5 ml or 25 µCi radiolabelled tracer [1-$^{14}$C] 18:3 ([$^{14}$C] trilinolenin, 50-60 mCi/mmol; 50 µCi/mL) was added to 4.56 g tuna oil. Two lots of tuna oil samples with radiolabelled trilinolenin were prepared, one for encapsulated oil treatment (see example 19 for formulation and manufacture) and one for free (unencapsulated) oil treatment.

Rat Treatment:

On the day of treatment rats were fed intra-gastrically using a stainless steel gavage needle either with 0.3 ml fish oil mixed with radiolabelled tracer [$^{14}$C] 18:3 (0.27 g tuna oil+0.03 ml tracer [$^{14}$C] 18:3) for control treatment or 2 ml emulsion (0.09 g tuna oil+0.01 ml tracer [$^{14}$C] 18:3) for the microencapsulated treatment.

Tissue Sampling:

At time points of 4, 9 and 14 hours following treatment, rats were anesthetised and a blood sample taken by cardiac puncture. The stomach, small intestine, caecum and colon were removed. The small intestine was divided into two sections, each GI tract segment was flushed with 0.9% NaCl and the washings collected and frozen. The GI tract segments were then frozen for subsequent analysis. Faeces were also collected for analysis at time points. The tissues and faeces were weighed and samples taken for analysis and weighed.

Tissue Sample Analysis:

Radioactivity of GI tract washings containing all unabsorbed oil (both released and encapsulated oil) was counted to estimate the total amount of radioactivity. Tissue samples were dissolved overnight in BTS-450® tissue solubiliser. Faecal matters were dissolved in BTS-450®, with some prior treatment. The liquid scintillation cocktail Ready Organic® was added to each sample and the sample subjected to liquid scintillation counting in a Packard 1500 Tri-Carb Scintillation Counter.

Example 1

Formulations and Manufacture of Powders with 25% Oil Loading with Unheated or Heated Blends of Protein-Glucose/Dried Glucose Syrup or Protein-Oligosaccharide as Encapsulants

| Ingredient | powder composition | emulsion composition | Processing steps |
|---|---|---|---|
| Water |  | 69.2% | Prepare NaCas solution (Alanate) at 60° C., add |
| Alanate 180 | 25.0% | 7.7% | sugars [glucose and DGS (Maltostar)], |
| Glucose•H$_2$O | 25.0% | 7.7% | (preferably, adjust pH of solution to 7.5, heat to |
| Maltostar 30 | 25.0% | 7.7% | 98° C. and hold for 30 minutes, cool down to |
| Tuna oil | 25.0% | 7.7% | 60° C.), add oil heated to 60° C., homogenise at |
| Total | 100.0% | 100.0% | 350/100 bar, spray dry at 180/80° C. Inlet temperature (Ti)/Outlet temperature (To). |
| Water |  | 69.2% | Prepare NaCas solution at 60° C., add |
| Alanate 180 | 25.0% | 7.7% | oligosaccharide, (preferably, adjust pH of |
| Raftilose P95 | 50.0% | 15.4% | solution to 7.5, heat to 98° C. and hold for 30 |
| Tuna oil | 25.0% | 7.7% | minutes, cool down to 60° C.), add oil heated to |
| Total | 100.0% | 100.0% | 60° C., homogenise at 350/100 bar, spray dry at 180/80° C. Ti/To. |
| Water |  | 69.2% | Prepare WPI solution (Alacen) at 60° C., add |
| Alacen 895 | 25.0% | 7.7% | sugars, (preferably, adjust pH of solution to 7.5, |
| Glucose.H$_2$O | 25.0% | 7.7% | heat to 98° C. and hold for 30 minutes, cool down |
| Maltostar 30 | 25.0% | 7.7% | to 60° C.), add oil heated to 60° C., homogenise at |
| Tuna oil | 25.0% | 7.7% | 350/100 bar, spray dry at 180/80° C. Ti/To. |
| Total | 100.0% | 100.0% |  |
| Water |  | 69.2% | Prepare WPI solution at 60° C., add |
| Alacen 895 | 25.0% | 7.7% | oligosaccharidesugars, (preferably, adjust pH of |
| Raftilose P95 | 50.0% | 15.4% | solution to 7.5, heat to 98° C. and hold for 30 |
| Tuna oil | 25.0% | 7.7% | minutes, cool down to 60° C.), add oil heated to |
| Total | 100.0% | 100.0% | 60° C., homogenise at 350/100 bar, spray dry at 180/80° C. Ti/To. |

Example 2

Formulations and Manufacture of Powders with 50% Oil Loading with Unheated or Heated Blends of Protein-Glucose/Dried Glucose Syrup or Protein-Oligosaccharide as Encapsulants

| Ingredient | powder composition | emulsion composition | Processing steps |
|---|---|---|---|
| Water |  | 60.0% | Prepare NaCas solution at 60° C., add sugars, |
| Alanate 180 | 16.7% | 6.7% | (preferably, adjust pH of solution to 7.5, heat to |
| Glucose•H$_2$O | 16.7% | 6.7% | 98° C. and hold for 30 minutes, cool down to |
| Maltostar 30 | 16.7% | 6.7% | 60° C.), add oil heated to 60° C., homogenise at |
| Tuna oil | 50.0% | 20.0% | 350/100 bar, spray dry at 180/80° C. Ti/To. |
| Total | 100.0% | 100.0% |  |

-continued

| Ingredient | powder composition | emulsion composition | Processing steps |
|---|---|---|---|
| Water | | 60.0% | Prepare NaCas solution at 60° C., add |
| Alanate 180 | 16.7% | 6.7% | oligosaccharide (Raftilose), (preferably, adjust pH |
| Raftilose P95 | 33.3% | 13.3% | of solution to 7.5, heat to 98° C. and hold for 30 |
| Tuna oil | 50.0% | 20.0% | minutes, cool down to 60° C.), add oil heated to |
| Total | 100.0% | 100.0% | 60° C., homogenise at 350/100 bar, spray dry at 180/80° C. Ti/To. |
| Water | | 60.0% | Prepare WPI solution at 60° C., add sugars, |
| Alacen 895 | 16.7% | 6.7% | (preferably, adjust pH of solution to 7.5, heat to |
| Glucose.H$_2$O | 16.7% | 6.7% | 98° C. and hold for 30 minutes, cool down to |
| Maltostar 30 | 16.7% | 6.7% | 60° C.), add oil heated to 60° C., homogenise at |
| Tuna oil | 50.0% | 20.0% | 350/100 bar, spray dry at 180/80° C. Ti/To. |
| Total | 100.0% | 100.0% | |
| Water | | 60.0% | Prepare WPI solution at 60° C., add |
| Alacen 895 | 16.7.0% | 6.7% | oligosaccharidesugars, (preferably, adjust pH of |
| Raftilose P95 | 33.3% | 13.3% | solution to 7.5, heat to 98° C. and hold for 30 |
| Tuna oil | 50.0% | 20.0% | minutes, cool down to 60° C.), add oil heated to |
| Total | 100.0% | 100.0% | 60° C., homogenise at 350/100 bar, spray dry at 180/80° C. Ti/To. |

Example 3

Formulations and Manufacture of Powders with 25% Oil Loading with Heated Blends of Protein-Starch as Encapsulants

| Ingredient | powder composition | emulsion composition | Processing steps |
|---|---|---|---|
| Water | | 69.2% | Prepare NaCas solution at 60° C., add starch |
| Alanate 180 | 25.0% | 7.7% | (Capsul), (preferably, adjust pH of solution to 7.5, |
| Capsul | 50.0% | 15.4% | heat to 98° C. and hold for 30 minutes, cool down |
| Tuna oil | 25.0% | 7.7% | to 60° C.), add oil heated to 60° C., homogenise at |
| Total | 100.0% | 100.0% | 350/100 bar, spray dry at 180/80° C. Ti/To. |
| Water | | 69.2% | Prepare NaCas solution at 60° C., add starch (Hi- |
| Alanate 180 | 25.0% | 7.7% | Cap), (preferably, adjust pH of solution to 7.5, |
| Hi-Cap 100 | 50.0% | 15.4% | heat to 98° C. and hold for 30 minutes, cool down |
| Tuna oil | 25.0% | 7.7% | to 60° C.), add oil heated to 60° C., homogenise at |
| Total | 100.0% | 100.0% | 350/100 bar, spray dry at 180/80° C. Ti/To. |
| Water | | 69.2% | Prepare NaCas solution at 60° C., add dextrin, |
| Alanate 180 | 25.0% | 7.7% | (preferably, adjust pH of solution to 7.5, heat to |
| Tapioca dextrin K4484 | 50.0% | 15.4% | 98° C. and hold for 30 minutes, cool down to 60° C.), add oil heated to 60° C., homogenise at |
| Tuna oil | 25.0% | 7.7% | 350/100 bar, spray dry at 180/80° C. Ti/To. |
| Total | 100.0% | 100.0% | |
| Water | | 69.2% | Prepare WPI solution at 60° C., add dextrin, |
| Alacen 895 | 25.0% | 7.7% | (preferably, adjust pH of solution to 7.5, heat to |
| Tapioca dextrin K4484 | 50.0% | 15.4% | 98° C. and hold for 30 minutes, cool down to 60° C.), add oil heated to 60° C., homogenise at |
| Tuna oil | 25.0% | 7.7% | 350/100 bar, spray dry at 180/80° C. Ti/To. |
| Total | 100.0% | 100.0% | |

Example 4

Formulations and Manufacture of Powders with 50% Oil Loading with Heated Blends of Protein-Starch as Encapsulants

| Ingredient | powder composition | emulsion composition | Processing steps |
|---|---|---|---|
| Water | | 60.0% | Prepare NaCas solution at 60° C., add starch, |
| Alanate 180 | 16.7% | 6.7% | (preferably, adjust pH of solution to 7.5, heat to |
| Capsul | 33.3% | 13.3% | 98° C. and hold for 30 minutes, cool down to |
| Tuna oil | 50.0% | 20.0% | 60° C.), add oil heated to 60° C., homogenise at |
| Total | 100.0% | 100.0% | 350/100 bar, spray dry at 180/80° C. Ti/To. |
| Water | | 60.0% | Prepare NaCas solution at 60° C., add starch, |
| Alanate 180 | 16.7% | 6.7% | (preferably, adjust pH of solution to 7.5, heat to |
| Hi-Cap 100 | 33.3% | 13.3% | 98° C. and hold for 30 minutes, cool down to |
| Tuna oil | 50.0% | 20.0% | 60° C.), add oil heated to 60° C., homogenise at |
| Total | 100.0% | 100.0% | 350/100 bar, spray dry at 180/80° C. Ti/To. |
| Water | | 60.0% | Prepare NaCas solution at 60° C., add dextrin, |
| Alanate 180 | 16.7% | 6.7% | (preferably, adjust pH of solution to 7.5, heat to |
| Tapioca dextrin K4484 | 33.3% | 13.3% | 98° C. and hold for 30 minutes, cool down to 60° C.), add oil heated to 60° C., homogenise at |
| Tuna oil | 50.0% | 20.0% | 350/100 bar, spray dry at 180/80° C. Ti/To. |
| Total | 100.0% | 100.0% | |
| Water | | 60.0% | Prepare WPI solution at 60° C., add dextrin, |
| Alacen 895 | 16.7% | 6.7% | (preferably, adjust pH of solution to 7.5, heat to |
| Tapioca dextrin K4484 | 33.3% | 13.3% | 98° C. and hold for 30 minutes, cool down to 60° C.), add oil heated to 60° C., homogenise at |
| Tuna oil | 50.0% | 20.0% | 350/100 bar, spray dry at 180/80° C. Ti/To. |
| Total | 100.0% | 100.0% | |

Example 5

Formulations and Manufacture of Powders with 25% Oil Loading with Heated Blends of Protein-Glucose/Glucose Syrup or Protein-Oligosaccharide in Combination with Gums as Encapsulants

| Ingredient | powder composition | emulsion composition | Processing steps |
|---|---|---|---|
| Water | | 69.2% | Prepare NaCas solution at 60° C., add sugars and |
| Alanate 180 | 25.0% | 7.7% | alginate (Protanal), (preferably, adjust pH of |
| Glucose•H$_2$O | 25.0% | 7.7% | solution to 7.5, heat to 98° C. and hold for 30 |
| Maltostar 30 | 22.5% | 6.9% | minutes, cool down to 60° C.), add oil heated to |
| Protanal | 2.5% | 0.8% | 60° C., homogenise at 350/100 bar, spray dry at |
| Tuna oil | 25.0% | 7.7% | 180/80° C. Ti/To. |
| Total | 100.0% | 100.0% | |
| Water | | 77.7% | Prepare NaCas solution at 60° C., add |
| Alanate 180 | 25.0% | 5.6% | oligosaccharide and guar gum solution, |
| Raftilose P95 | 48.75% | 10.9% | (preferably, adjust pH of solution to 7.5, heat to |
| Guar WW250F | 1.25% | 0.3% | 98° C. and hold for 30 minutes, cool down to 60° C.), add oil heated to 60° C., homogenise at |
| Tuna oil | 25.0% | 5.6% | 350/100 bar, spray dry at 180/80° C. Ti/To. |
| Total | 100.0% | 100.0% | |
| Water | | 73.2% | Prepare NaCas solution at 60° C., add |
| Alanate 180 | 25.0% | 6.7% | oligosaccharide and carrageenan solution |
| Raftilose P95 | 48.75% | 13.0% | (Gelcarin), (preferably, adjust pH of solution to |
| Gelcarin GP 812 | 1.25% | 0.3% | 7.5, heat to 98° C. and hold for 30 minutes, cool down to 60° C., add oil heated to 60° C., |
| Tuna oil | 25.0% | 6.7% | homogenise at 350/100 bar, spray dry at |
| Total | 100.0% | 100.0% | 180/80° C. Ti/To. |
| Water | | 73.1% | Prepare NaCas solution at 60° C., add |
| Alanate 180 | 25.0% | 6.7% | oligosaccharide and high methoxy pectin (HMP) |

| Ingredient | powder composition | emulsion composition | Processing steps |
|---|---|---|---|
| Raftilose P95 | 47.5% | 12.7% | solution, (preferably, adjust pH of solution to 7.5, |
| HMP RS400 | 2.5% | 0.7% | heat to 98° C. and hold for 30 minutes, cool down |
| Tuna oil | 25.0% | 6.7% | to 60° C.), add oil heated to 60° C., homogenise at |
| Total | 100.0% | 100.0% | 350/100 bar, spray dry at 180/80° C. Ti/To. |
| Water | | 73.1% | Prepare NaCas solution at 60° C., add glucose- |
| Alacen 895 | 25.0% | 6.7% | DGS and high methoxy pectin (HMP) solution, |
| 1:1 Glu:DGS | 47.5% | 12.7% | (preferably, adjust pH of solution to 7.5, heat to |
| HMP RS400 | 2.5% | 0.7% | 98° C. and hold for 30 minutes, cool down to |
| Tuna oil | 25.0% | 6.7% | 60° C.), add oil heated to 60° C., homogenise at |
| Total | 100.0% | 100.0% | 350/100 bar, spray dry at 180/80° C. Ti/To. |
| Water | | 77.7% | Prepare WPI solution at 60° C., add |
| Alacen 895 | 25.0% | 5.6% | oligosaccharide and guar gum solution, |
| Raftilose P95 | 48.75% | 10.9% | (preferably, adjust pH of solution to 7.5, heat to |
| Guar WW250F | 1.25% | 0.3% | 98° C. and hold for 30 minutes, cool down to 60° C.), add oil heated to 60° C., homogenise at |
| Tuna oil | 25.0% | 5.6% | 350/100 bar, spray dry at 180/80° C. Ti/To. |
| Total | 100.0% | 100.0% | |
| Water | | 73.2% | Prepare NaCas solution at 60° C., add |
| Alacen 895 | 25.0% | 6.7% | oligosaccharide and 60° C. carrageenan solution, |
| Raftilose P95 | 48.75% | 13.0% | (preferably, adjust pH of solution to 7.5, heat to |
| Gelcarin GP 812 | 1.25% | 0.3% | 98° C. and hold for 30 minutes, cool down to 60° C.), add oil heated to 60° C., homogenise at |
| Tuna oil | 25.0% | 6.7% | 350/100 bar, spray dry at 180/80° C. Ti/To. |
| Total | 100.0% | 100.0% | |
| water | | 73.1% | Prepare NaCas solution at 60° C., add |
| Alacen 895 | 25.0% | 6.7% | oligosaccharide and 60° C. HMP solution, |
| Raftilose P95 | 47.5% | 12.7% | (preferably, adjust pH of solution to 7.5, heat to |
| HMP RS400 | 2.5% | 0.7% | 98° C. and hold for 30 minutes, cool down to |
| Tuna oil | 25.0% | 6.7% | 60° C.), add oil heated to 60° C., homogenise at |
| Total | 100.0% | 100.0% | 350/100 bar, spray dry at 180/80° C. Ti/To. |

Example 6

Formulations and Manufacture of Powders with 50% Oil Loading with Heated Blends of Protein-Glucose/Glucose Syrup or Protein-Oligosaccharide in Combination with Gums as Encapsulants

| Ingredient | powder composition | emulsion composition | Processing steps |
|---|---|---|---|
| water | | 60.0% | Prepare NaCas solution at 60° C., add sugars and |
| Alanate 180 | 16.7% | 6.7% | alginate, (preferably, adjust pH of solution to 7.5, |
| Glucose | 16.7% | 6.7% | heat to 98° C. and hold for 30 minutes, cool down |
| Maltostar 30 | 15.0% | 6.0% | to 60° C.), add oil heated to 60° C., homogenise at |
| Protanal | 1.7% | 0.7% | 350/100 bar, spray dry at 180/80° C. Ti/To. |
| Tuna oil | 50.0% | 20.0% | |
| Total | 100.0% | 100.0% | |
| Water | | 69.9% | Prepare HWP solution at 60° C., add |
| NaCas | 16.7% | 5.0% | oligosaccharide and guar gum solution, |
| Raftilose P95 | 32.5% | 9.8% | (preferably, adjust pH of solution to 7.5, heat to |
| Guar WW250F | 0.8% | 0.3% | 98° C. and hold for 30 minutes, cool down to 60° C.), add oil heated to 60° C., homogenise at |
| Tuna oil | 50.0% | 15.0% | 350/100 bar, spray dry at 180/80° C. Ti/To. |
| Total | 100.0% | 100.0% | |
| Water | | 64.6% | Prepare NaCas solution at 60° C., add |
| Alanate 180 | 16.7% | 5.9% | oligosaccharide and carrageenan solution, |
| Raftilose P95 | 32.5% | 11.5% | (preferably, adjust pH of solution to 7.5, heat to |
| Gelcarin GP 812 | 0.8% | 0.3% | 98° C. and hold for 30 minutes, cool down to 60° C.), add oil heated to 60° C., homogenise at |
| Tuna oil | 50.0% | 17.7% | 350/100 bar, spray dry at 180/80° C. Ti/To. |
| Total | 100.0% | 100.0% | |

-continued

| Ingredient | powder composition | emulsion composition | Processing steps |
|---|---|---|---|
| Water | | 64.5% | Prepare NaCas solution at 60° C., add |
| Alanate 180 | 16.7% | 5.9% | oligosaccharidesugars and HMP solution, |
| Raftilose P95 | 31.7% | 11.2% | (preferably, adjust pH of solution to 7.5, heat to |
| HMP RS400 | 1.7% | 0.6% | 98° C. and hold for 30 minutes, cool down to |
| Tuna oil | 50.0% | 17.8% | 60° C.), add oil heated to 60° C., homogenise at |
| Total | 100.0% | 100.0% | 350/100 bar, spray dry at 180/80° C. Ti/To. |
| Water | | 69.9% | Prepare WPI solution at 60° C., add |
| Alacen 895 | 16.7% | 5.0% | oligosaccharide and guar gum solution, |
| Raftilose P95 | 32.5% | 9.8% | (preferably, adjust pH of solution to 7.5, heat to |
| Guar WW250F | 0.8% | 0.3% | 98° C. and hold for 30 minutes, cool down to 60° C.), add oil heated to 60° C., homogenise at |
| Tuna oil | 50.0% | 15.0% | 350/100 bar, spray dry at 180/80° C. Ti/To. |
| Total | 100.0% | 100.0% | |
| Water | | 53.1% | Prepare WPI solution at 60° C., add |
| Alacen 895 | 16.7% | 5.9% | oligosaccharide and carrageenan solution, |
| Raftilose P95 | 32.5% | 11.5% | (preferably, adjust pH of solution to 7.5, heat to |
| Gelcarin GP 812 | 0.8% | 0.3% | 98° C. and hold for 30 minutes, cool down to 60° C.), add oil heated to 60° C., homogenise at |
| Water for gum dispersion | | 11.5% | 350/100 bar, spray dry at 180/80° C. Ti/To. |
| Tuna oil | 50.0% | 17.7% | |
| Total | 100.0% | 100.0% | |
| Water | | 53.3% | Prepare WPI solution at 60° C., add |
| Alacen 895 | 16.7% | 5.9% | oligosaccharide and 60° C. HMP solution, |
| Raftilose P95 | 31.7% | 11.2% | (preferably, adjust pH of solution to 7.5, heat to |
| HMP RS400 | 1.7% | 0.6% | 98° C. and hold for 30 minutes, cool down to |
| Water for gum dispersion | | 11.2% | 60° C.), add oil heated to 60° C., homogenise at 350/100 bar, spray dry at 180/80° C. Ti/To. |
| Tuna oil | 50.0% | 17.8% | |
| Total | 100.0% | 100.0% | |

Example 7

Formulations and Manufacture of Powders with 25% Oil Loading with Heated Blends of Protein Hydrolysate-Oligosaccharide in Combination with Gums as Encapsulants

| Ingredient | powder composition | emulsion composition | Processing steps |
|---|---|---|---|
| Water | | 73.2% | Prepare hydrolysed casein protein (HCP) |
| HCP 102 | 25.0% | 6.7% | solution at 60° C., add oligosaccharide, and 60° C. |
| Raftilose P95 | 48.75% | 13.0% | carrageenan solution (preferably, adjust pH of |
| Gelcarin GP 812 | 1.25% | 0.3% | solution to 7.5, heat to 98° C. and hold for 30 minutes, cool down to 60° C.), add oil heated to |
| Tuna oil | 25.0% | 6.7% | 60° C., homogenise at 350/100 bar, spray dry at |
| Total | 100.0% | 100.0% | 180/80° C. Ti/To. |
| Water | | 73.1% | Prepare HCP solution at 60° C., add |
| HCP 102 | 25.0% | 6.7% | oligosaccharide and HMP solution, (preferably, |
| Raftilose P95 | 47.5% | 12.7% | adjust pH of solution to 7.5, heat to 98° C. and |
| HMP RS400 | 2.5% | 0.7% | hold for 30 minutes, cool down to 60° C.), add oil |
| Tuna oil | 25.0% | 6.7% | heated to 60° C., homogenise at 350/100 bar, |
| Total | 100.0% | 100.0% | spray dry at 180/80° C. Ti/To. |
| Water | | 73.2% | Prepare hydrolysed whey protein (HWP) solution |
| HWP 205 | 25.0% | 6.7% | at 60° C., add oligosaccharide and carrageenan |
| Raftilose P95 | 48.75% | 13.0% | solution, (preferably, adjust pH of solution to 7.5, |
| Gelcarin GP 812 | 1.25% | 0.3% | heat to 98° C. and hold for 30 minutes, cool down to 60° C.), add oil heated to 60° C., homogenise at |
| Tuna oil | 25.0% | 6.7% | 350/100 bar, spray dry at 180/80° C. Ti/To. |
| Total | 100.0% | 100.0% | |
| Water | | 73.1% | Prepare HWP solution at 60° C., add |
| HWP 205 | 25.0% | 6.7% | oligosaccharide and HMP solution, (preferably, |

-continued

| Ingredient | powder composition | emulsion composition | Processing steps |
|---|---|---|---|
| Raftilose P95 | 47.5% | 12.7% | adjust pH of solution to 7.5, heat to 98° C. and |
| HMP RS400 | 2.5% | 0.7% | hold for 30 minutes, cool down to 60° C.), add oil |
| Tuna oil | 25.0% | 6.7% | heated to 60° C., homogenise at 350/100 bar, |
| Total | 100.0% | 100.0% | spray dry at 180/80° C. Ti/To. |
| Water | | 73.1% | Prepare HWP solution at 60° C., add glucose- |
| HWP 205 | 25.0% | 6.7% | DGS and HMP solution, (preferably, adjust pH of |
| 1:1 Glu: DGS | 47.5% | 12.7% | solution to 7.5, heat to 98° C. and hold for 30 |
| HMP RS400 | 2.5% | 0.7% | minutes, cool down to 60° C.), add oil heated to |
| Tuna oil | 25.0% | 6.7% | 60° C., homogenise at 350/100 bar, spray dry at |
| Total | 100.0% | 100.0% | 180/80° C. Ti/To. |

Example 8

Formulations and Manufacture of Powders with 50% Oil Loading with Heated Blends of Hydrolysate-Oligosaccharide in Combination with Gums as Encapsulants

| Ingredient | powder composition | emulsion composition | Processing steps |
|---|---|---|---|
| Water | | 64.6% | Prepare HCP solution at 60° C., add |
| HCP 102 | 16.7% | 5.9% | oligosaccharide and carrageenan solution, |
| Raftilose P95 | 32.5% | 11.5% | (preferably, adjust pH of solution to 7.5, heat to |
| Gelcarin GP 812 | 0.8% | 0.3% | 98° C. and hold for 30 minutes, cool down to 60° C.), add oil heated to 60° C., homogenise at |
| Tuna oil | 50.0% | 17.7% | 350/100 bar, spray dry at 180/80° C. Ti/To. |
| Total | 100.0% | 100.0% | |
| Water | | 64.5% | Prepare HCP solution at 60° C., add |
| HCP 102 | 16.7% | 5.9% | oligosaccharide and HMP solution, (preferably, |
| Raftilose P95 | 31.7% | 11.2% | adjust pH of solution to 7.5, heat to 98° C. and |
| HMP RS400 | 1.7% | 0.6% | hold for 30 minutes, cool down to 60° C.), add oil |
| Tuna oil | 50.0% | 17.8% | heated to 60° C., homogenise at 350/100 bar, |
| Total | 100.0% | 100.0% | spray dry at 180/80° C. Ti/To. |
| Water | | 64.6% | Prepare HWP solution at 60° C., add |
| HWP 205 | 16.7% | 5.9% | oligosaccharide and carrageenan solution, |
| Raftilose P95 | 32.5% | 11.5% | (preferably, adjust pH of solution to 7.5, heat to |
| Gelcarin GP 812 | 0.8% | 0.3% | 98° C. and hold for 30 minutes, cool down to 60° C.), add oil heated to 60° C., homogenise at |
| Tuna oil | 50.0% | 17.7% | 350/100 bar, spray dry at 180/80° C. Ti/To. |
| Total | 100.0% | 100.0% | |
| Water | | 64.5% | Prepare HWP solution at 60° C., add |
| HWP 205 | 16.7% | 5.9% | oligosaccharide and HMP solution, (preferably, |
| Raftilose P95 | 31.7% | 11.2% | adjust pH of solution to 7.5, heat to 98° C. and |
| HMP RS400 | 1.7% | 0.6% | hold for 30 minutes, cool down to 60° C.), add oil |
| Tuna oil | 50.0% | 17.8% | heated to 60° C., homogenise at 350/100 bar, |
| Total | 100.0% | 100.0% | spray dry at 180/80° C. Ti/To. |

Example 9

Formulations and Manufacture of Powders with 25% Oil Loading with Blends of Sodium Caseinate with Raw or Processed Resistant Starch (Potato Starch)

| Ingredient | powder composition | emulsion composition | |
|---|---|---|---|
| | | | Processing steps (using raw potato starch) |
| Water | | 84.6% | Prepare 10% TS starch dispersion at 70° C. |
| Potato starch | 37.5% | 5.8% | Prepare 15% TS NaCas solution at 60° C. and mix |
| Alanate 180 | 37.5% | 5.8% | with starch dispersion above. (Preferably heat |
| Tuna oil | 25.0% | 3.8% | protein-starch mixture in cans at 98° C.-30 |
| Total | 100.0% | 100.0% | minutes, cool down to 60° C.). Add oil heated to 60° C., homogenise at 350/100 bar, spray dry at 180/80° C. Ti/To. |
| | | | Processing steps (using heat processed potato starch) |
| Water | | 84.6% | Prepare 10% TS starch dispersion at 70° C., |
| Potato starch | 37.5% | 5.8% | process in 73 × 82 mm cans at 121° C.-60 |
| Alanate 180 | 37.5% | 5.8% | minutes, cool down. Prepare 15% TS NaCas |
| Tuna oil | 25.0% | 3.8% | solution at 60° C. and mix with processed starch |
| Total | 100.0% | 100.0% | above. (Preferably heat protein-starch mixture in cans at 98° C.-30 minutes, cool down to 60° C.). Add oil heated to 60° C., homogenise at 350/100 bar, spray dry at 180/80° C. Ti/To. |
| | | | Processing steps (using heat processed and microfluidised potato starch) |
| Water | | 84.6% | Prepare 10% TS starch dispersion at 70° C., |
| Potato starch | 37.5% | 5.8% | process in 73 × 82 mm cans at 121° C.-60 |
| Alanate 180 | 37.5% | 5.8% | minutes, cool down, microfluidise at 800 bar-3 |
| Tuna oil | 25.0% | 3.8% | passes. Prepare 15% TS NaCas solution at 60° C. |
| Total | 100.0% | 100.0% | and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. |
| | | | Processing steps (using extruded potato starch) |
| Water | | 84.6% | Prepare 10% TS extruded starch dispersion at |
| Potato starch | 37.5% | 5.8% | 70° C. Prepare 15% TS NaCas solution at 60° C. |
| Alanate 180 | 37.5% | 5.8% | and mix with starch dispersion above. |
| Tuna oil | 25.0% | 3.8% | (Preferably heat protein-starch mixture in cans at |
| Total | 100.0% | 100.0% | 98° C.-30 minutes, cool down to 60° C.). Add oil heated to 60° C., homogenise at 350/100 bar, spray dry at 180/80° C. Ti/To. |

Example 10

Formulations and Manufacture of Powders with 25% Oil Loading with Blends of Sodium Caseinate with Hylon VII or Pre-Processed Resistant Starch (Hylon VII)

| Ingredient | powder composition | emulsion composition | |
|---|---|---|---|
| | | | Processing steps (using Hylon VII starch) |
| Water | | 84.6% | Prepare 10% TS starch dispersion at 70° C. |
| Hylon VII | 37.5% | 5.8% | Prepare 15% TS NaCas solution at 60° C. and mix |
| Alanate 180 | 37.5% | 5.8% | with starch dispersion above. (Preferably heat |
| Tuna oil | 25.0% | 3.8% | protein-starch mixture in cans at 98° C.-30 |
| Total | 100.0% | 100.0% | minutes, cool down to 60° C.). Add oil heated to |

-continued

| Ingredient | powder composition | emulsion composition | |
|---|---|---|---|
| | | | 60° C., homogenise at 350/100 bar, spray dry at 180/80° C. Ti/To.<br>Processing steps (using heat processed Hylon VII starch) |
| Water | | 84.6% | Prepare 20% TS starch dispersion at 70° C., |
| Hylon VII | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS Prepare 15% TS NaCas |
| Total | 100.0% | 100.0% | solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To.<br>Processing steps (using heat processed and microfluidised Hylon VII starch) |
| Water | | 84.6% | Prepare 20% TS starch dispersion at 70° C., |
| Hylon VII | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To.<br>Processing steps (using extruded Hylon VII starch) |
| Water | | 84.6% | Prepare 10% TS extruded starch dispersion at |
| Hylon VII | 37.5% | 5.8% | 70° C. Prepare 15% TS NaCas solution at 60° C. |
| Alanate 180 | 37.5% | 5.8% | and mix with starch dispersion above. |
| Tuna oil | 25.0% | 3.8% | (Preferably heat protein-starch mixture in cans at |
| Total | 100.0% | 100.0% | 98° C.-30 minutes, cool down to 60° C.). Add oil heated to 60° C., homogenise at 350/100 bar, spray dry at 180/80° C. Ti/To. |

Example 11

Formulations and Manufacture of Powders with 25% Oil Loading with Blends of Sodium Caseinate with Hi-Maize 1043 or Pre-Processed Resistant Starch (Hi-Maize 1043)

| Ingredient | powder composition | emulsion composition | |
|---|---|---|---|
| | | | Processing steps (using Hi-Maize starch) |
| Water | | 84.6% | Prepare 10% TS starch dispersion at 70° C.. |
| Hi-Maize 1043 | 37.5% | 5.8% | Prepare 15% TS NaCas solution at 60° C. and mix |
| Alanate 180 | 37.5% | 5.8% | with starch dispersion above. (Preferably heat |
| Tuna oil | 25.0% | 3.8% | protein-starch mixture in cans at 98° C.-30 |
| Total | 100.0% | 100.0% | minutes, cool down to 60° C.). Add oil heated to 60° C., homogenise at 350/100 bar, spray dry at 180/80° C. Ti/To.<br>Processing steps (using heat processed Hi-Maize starch) |
| Water | | 84.6% | Prepare 20% TS starch dispersion at 60° C., |
| Hi-Maize 1043 | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS. Prepare 15% TS NaCas |
| Total | 100.0% | 100.0% | solution at 60° C. and mix with processed starch above. (Preferably heat protein-starch mixture in cans at 98° C.-30 minutes, cool down to 60° C.). |

-continued

| Ingredient | powder composition | emulsion composition | |
|---|---|---|---|
| | | | Add oil heated to 60° C., homogenise at 350/100 bar, spray dry at 180/80° C. Ti/To. Processing steps (using heat processed and microfluidised Hi-Maize starch) |
| Water | | 84.6% | Prepare 20% TS starch dispersion at 70° C., |
| Hi-Maize 1043 | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. Processing steps (using extrude Hi-Maize starch) |
| Water | | 84.6% | Prepare 10% TS extruded starch dispersion at |
| Hi-Maize 1043 | 37.5% | 5.8% | 70° C.. Prepare 15% TS NaCas solution at 60° C. |
| Alanate 180 | 37.5% | 5.8% | and mix with starch dispersion above. |
| Tuna oil | 25.0% | 3.8% | (Preferably heat protein-starch mixture in cans at |
| Total | 100.0% | 100.0% | 98° C.-30 minutes, cool down to 60° C.). Add oil heated to 60° C., homogenise at 350/100 bar, spray dry at 180/80° C. Ti/To. |

Example 12

Formulations and Manufacture of Powders with 25% Oil Loading with Blends of Sodium Caseinate with Novelose 260 or Pre-Processed Resistant Starch (Novelose 260)

| Ingredient | powder composition | emulsion composition | |
|---|---|---|---|
| | | | Processing steps (using Novelose 260 starch) |
| Water | | 84.6% | Prepare 10% TS starch dispersion at 70° C.. |
| Novelose 260 | 37.5% | 5.8% | Prepare 15% TS NaCas solution at 60° C. and mix |
| Alanate 180 | 37.5% | 5.8% | with starch dispersion above. (Preferably heat |
| Tuna oil | 25.0% | 3.8% | protein-starch mixture in cans at 98° C.-30 |
| Total | 100.0% | 100.0% | minutes, cool down to 60° C.). Add oil heated to 60° C. homogenise at 350/100 bar, spray dry at 180/80° C. Ti/To. Processing steps (using heat processed Novelose 260 starch) |
| Water | | 84.6% | Prepare 20% TS starch dispersion at 70° C., |
| Novelose 260 | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS. Prepare 15% TS NaCas |
| Total | 100.0% | 100.0% | solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. Processing steps (using heat processed and microfluidised Novelose 260 starch) |
| Water | | 84.6% | Prepare 20% TS starch dispersion at 70° C., |
| Novelose 260 | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at |

-continued

| Ingredient | powder composition | emulsion composition | |
|---|---|---|---|
| | | | 98° C.-30 minutes, cool down to 60° C.). Add oil heated to 60° C., homogenise at 350/100 bar, spray dry at 180/80° C. Ti/To. |
| | | | Processing steps |
| Water | | 84.6% | Prepare 10% TS extruded starch dispersion at |
| Novelose 260 | 37.5% | 5.8% | 70° C.. Prepare 15% TS NaCas solution at 60° C. |
| Alanate 180 | 37.5% | 5.8% | and mix with starch dispersion above. |
| Tuna oil | 25.0% | 3.8% | (Preferably heat protein-starch mixture in cans at |
| Total | 100.0% | 100.0% | 98° C.-30 minutes, cool down to 60° C.). Add oil heated to 60° C., homogenise at 350/100 bar, spray dry at 180/80° C. Ti/To. |

Example 13

Formulations and Manufacture of Powders with 25% Oil Loading with Blends of Sodium Caseinate with Novelose 330 or Pre-Processed Resistant Starch (Novelose 330)

| Ingredient | powder composition | emulsion composition | |
|---|---|---|---|
| | | | Processing steps (using Novelose 330 starch) |
| Water | | 84.6% | Prepare 10% TS starch dispersion at 70° C.. |
| Novelose 330 | 37.5% | 5.8% | Prepare 15% TS NaCas solution at 60° C. and mix |
| Alanate 180 | 37.5% | 5.8% | with starch dispersion above. (Preferably heat |
| Tuna oil | 25.0% | 3.8% | protein-starch mixture in cans at 98° C.-30 |
| Total | 100.0% | 100.0% | minutes, cool down to 60° C.). Add oil heated to 60° C., homogenise at 350/100 bar, spray dry at 180/80° C. Ti/To. |
| | | | Processing steps (using heat processed Novelose 330 starch) |
| Water | | 84.6% | Prepare 20% TS starch dispersion at 70° C., |
| Novelose 330 | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS. Prepare 15% TS NaCas |
| Total | 100.0% | 100.0% | solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. |
| | | | Processing steps (using heat processed and microfluidised Novelose 330 starch) |
| Water | | 84.6% | Prepare 20% TS starch dispersion at 70° C., |
| Novelose 330 | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. |
| | | | Processing steps (using extruded Novelose 330 starch) |
| Water | | 84.6% | Prepare 10% TS extruded starch dispersion at |
| Novelose 330 | 37.5% | 5.8% | 70° C.. Prepare 15% TS NaCas solution at 60° C. |

-continued

| Ingredient | powder composition | emulsion composition | |
|---|---|---|---|
| Alanate 180 | 37.5% | 5.8% | and mix with starch dispersion above. |
| Tuna oil | 25.0% | 3.8% | (Preferably heat protein-starch mixture in cans at |
| Total | 100.0% | 100.0% | 98° C.-30 minutes, cool down to 60° C.). Add oil heated to 60° C., homogenise at 350/100 bar, spray dry at 180/80° C. Ti/To. |

Example 14

Formulations and Manufacture of Powders with 25% Oil Loading with Blends of Sodium Caseinate with Hylon VII or High Pressure Processed or Ultrasonicated Resistant Starch (Hylon VII)

| Ingredient | powder composition | emulsion composition | |
|---|---|---|---|
| | | | Processing steps (using Hylon VII starch) |
| Water | | 84.6% | Prepare 10% TS starch dispersion at 70° C. |
| Hylon VII | 37.5% | 5.8% | Prepare 15% TS NaCas solution at 60° C. and mix |
| Alanate 180 | 37.5% | 5.8% | with starch dispersion above. (Preferably heat |
| Tuna oil | 25.0% | 3.8% | protein-starch mixture in cans at 98° C.-30 |
| Total | 100.0% | 100.0% | minutes, cool down to 60° C.). Add oil heated to 60° C., homogenise at 350/100 bar, spray dry at 180/80° C. Ti/To.<br>Processing steps (using heat processed and microfluidised x1 pass Hylon VII starch) |
| Water | | 84.6% | Prepare 20% TS starch dispersion at 70° C., |
| Hylon VII | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-1 |
| Total | 100.0% | 100.0% | pass. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bars, spray dry at 180/80° C. Ti/To.<br>Processing steps (using heat processed and microfluidised x3 pass Hylon VII starch) |
| Water | | 84.6% | Prepare 20% TS starch dispersion at 70° C., |
| Hylon VII | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bars, spray dry at 180/80° C. Ti/To.<br>Processing steps (using extruded Hylon VII starch) |
| Water | | 84.6% | Prepare 10% TS extruded starch dispersion at |
| Hylon VII | 37.5% | 5.8% | 70° C.. Prepare 15% TS NaCas solution at 60° C. |
| Alanate 180 | 37.5% | 5.8% | and mix with starch dispersion above. |
| Tuna oil | 25.0% | 3.8% | (Preferably heat protein-starch mixture in cans at |
| Total | 100.0% | 100.0% | 98° C.-30 minutes, cool down to 60° C.). Add oil heated to 60° C., homogenise at 350/100 bars, spray dry at 180/80° C. Ti/To.<br>Processing steps (using high pressure treated Hylon VII starch) |
| Water | | 84.6% | Prepare 20% TS starch dispersion at 70° C., |
| Hylon VII | 37.5% | | process in 73 × 82 mm cans at 121° C.-60 |

-continued

| Ingredient | powder composition | emulsion composition | |
|---|---|---|---|
| Alanate 180 | 37.5% | 5.8% | minutes, cool down, add remaining water to |
| Tuna oil | 25.0% | 3.8% | make-up to 10% TS, HPP at 600 MPa, for 15 |
| Total | 100.0% | 100.0% | minutes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. Processing steps (using ultrasound treated Hylon VII starch) |
| Water | | 84.6% | Prepare 20% TS starch dispersion at 70° C., |
| Hylon VII | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, US using 20 KHz unit @ 50 |
| Total | 100.0% | 100.0% | ml per minute, 380 Watts. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. |

Example 15

Formulations and Manufacture of Powders with 25% Oil Loading with Unheated and Heated Blends of Sodium Caseinate with Raw Starches or Pre-Processed Starch

| Ingredient | powder composition | emulsion composition | Processing steps |
|---|---|---|---|
| Water | | 84.6% | Prepare 10% TS starch dispersion at 70° C.. |
| Waxy maize | 37.5% | 5.8% | Prepare 15% TS NaCas solution at 60° C. and |
| Alanate 180 | 37.5% | 5.8% | mix with starch dispersion above. |
| Tuna oil | 25.0% | 3.8% | (Preferably heat protein-starch mixture in |
| Total | 100.0% | 100.0% | cans at 98° C.-30 minutes, cool down to 60° C.). Add oil heated to 60° C., homogenise at 350/100 bar, spray dry at 180/80° C. Ti/To. |
| Water | | 84.6% | Prepare 20% TS starch dispersion at 70° C., |
| Waxy maize | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, Microfluidise at 800 |
| Total | 100.0% | 100.0% | bar-1 pass. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. |
| Water | | 84.6% | Prepare 10% TS starch dispersion at 70° C.. |
| Maize starch | 37.5% | 5.8% | Prepare 15% TS NaCas solution at 60° C. and |
| Alanate 180 | 37.5% | 5.8% | mix with starch dispersion above. |
| Tuna oil | 25.0% | 3.8% | (Preferably heat protein-starch mixture in |
| Total | 100.0% | 100.0% | cans at 98° C.-30 minutes, cool down to 60° C.). Add oil heated to 60° C., homogenise at 350/100 bar, spray dry at 180/80° C. Ti/To. |
| Water | | 84.6% | Prepare 20% TS starch dispersion at 70° C., |
| Maize starch | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, Microfluidise at 800 bar-1 pass. Prepare 15% TS NaCas solution at 60° C. and mix with processed starch above. (Preferably heat protein-starch mixture in cans at 98° C.-30 minutes, cool down to 60° C.) Add oil heated to 60° C., |

-continued

| Ingredient | powder composition | emulsion composition | Processing steps |
|---|---|---|---|
| | | | homogenise at 350/100 bar, spray dry at 180/80° C. Ti/To. |
| Water | | 84.6% | Prepare 10% TS starch dispersion at 70° C., |
| Wheat starch | 37.5% | 5.8% | Prepare 15% TS NaCas solution at 60° C. and |
| Alanate 180 | 37.5% | 5.8% | mix with starch dispersion above. |
| Tuna oil | 25.0% | 3.8% | (Preferably heat protein-starch mixture in |
| Total | 100.0% | 100.0% | cans at 98° C.-30 minutes, cool down to 60° C.) Add oil heated to 60° C., homogenise at 350/100 bar, spray dry at 180/80° C. Ti/To. |
| Water | | 84.6% | Prepare 20% TS starch dispersion at 70° C., |
| Wheat starch | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, Microfluidise at 800 |
| Total | 100.0% | 100.0% | bar-1 pass. Prepare 15% TS NaCas solution at 60° C. and mix with processed starch above. (Preferably heat protein-starch mixture in cans at 98° C.-30 minutes, cool down to 60° C.) Add oil heated to 60° C., homogenise at 350/100 bar, spray dry at 180/80° C. Ti/To. |

Example 16

Formulations and Manufacture of Powders with 25% (Lutein-in-Oil) in Heated and Unheated Blends of Protein-Sugar-Starch as Encapsulants

| Ingredient | powder composition | emulsion composition | Processing steps |
|---|---|---|---|
| Water | | 69.2% | Prepare NaCas solution at 60° C., add DGS and |
| Alanate 180 | 25.0% | 7.7% | starch, (preferably, adjust pH of solution to 7.5, |
| Maltostar 30 | 25.0% | 7.7% | heat to 98° C. and hold for 30 minutes, cool down |
| Tapioca dextrin K4484 | 25.0% | 7.7% | to 60° C.), add lutein heated to 90° C., homogenise at 350/100 bars, spray dry at 180/80° C. Ti/To. |
| Lutein in oil | 25.0% | 7.7% | |
| Total | 100.0% | 100.0% | |

Example 17

Formulations and Manufacture of Powders with 25% Tributyrin in Heated Blends of Protein-Sugar or Protein-Sugar-RS Starch as Encapsulants

| Ingredient | powder composition | emulsion composition | |
|---|---|---|---|
| | | | Processing steps |
| Water | | 69.2% | Prepare NaCas solution at 60° C., add sugars, |
| Alanate 180 | 25.0% | 7.7% | (preferably, adjust pH of solution to 7.5, heat to |
| Glucose | 25.0% | 7.7% | 98° C. and hold for 30 minutes, cool down to |
| Maltostar 30 | 25.0% | 7.7% | 60° C.), add tributyrin, homogenise at 350/100 bar, spray dry at 180/80° C. Ti/To. |
| Tributyrin | 25.0% | 7.7% | |
| Total | 100.0% | 100.0% | |
| | | | Processing steps (using heat processed and microfluidised Hylon VII starch) |
| Water | | 69.2% | Prepare 20% TS starch dispersion at 70° C., |
| Alanate 180 | 25.0% | 7.7% | process in 73 × 82 mm cans at 121° C.-60 |
| Glucose | 25.0% | 7.7% | minutes, cool down, add remaining water to |

-continued

| Ingredient | powder composition | emulsion composition | |
|---|---|---|---|
| Hylon VII | 25.0% | 7.7% | make-up to 10% TS, microfluidise at 800 bar-3 |
| Tributyrin | 25.0% | 7.7% | passes. Prepare 15% TS NaCas solution at |
| Total | 100.0% | 100.0% | 60° C., add sugar and mix with processed starch above. (Preferably heat protein-starch mixture in cans at 98° C.-30 minutes, cool down to 60° C.). Add tributyrin, homogenise at 350/100 bars, spray dry at 180/80° C. Ti/To. |

Example 18

Formulations and Manufacture of Powders with 25% Tuna Oil in Heated Blends of NaCas-Sugar-HylonMF or NaCas-HylonMF or NaCas-StarPlus MF as Encapsulants

| Ingredient | powder composition | emulsion composition | |
|---|---|---|---|
| | | | Processing steps (using heat processed and microfluidised Hylon VII starch) |
| Water | | 69.2% | Prepare 20% TS starch dispersion at 70° C., |
| Alanate 180 | 25.0% | 7.7% | process in 73 × 82 mm cans at 121° C.-60 |
| Glucose | 25.0% | 7.7% | minutes, cool down, add remaining water to |
| Hylon VII | 25.0% | 7.7% | make-up to 10% TS, microfluidise at 800 bar-3 |
| Tuna oil | 25.0% | 7.7% | passes. Prepare 15% TS NaCas solution at |
| Total | 100.0% | 100.0% | 60° C., add sugar and mix with processed starch above. (Preferably heat protein-starch mixture in cans at 98° C.-30 minutes, cool down to 60° C.). Add tuna oil, homogenise at 350/100 bars, spray dry at 180/80° C. Ti/To. Processing steps (using heat processed and microfluidised Hylon VII starch) |
| Water | | 84.6% | Prepare 20% TS starch dispersion at 70° C., |
| Hylon VII | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. Processing steps (using heat processed and microfluidised Star Plus A) |
| Water | | 84.6% | Prepare 20% TS Star Plus A dispersion at 70° C., |
| Star Plus A | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. (Preferably heat protein-starch mixture in cans at 98° C.-30 minutes, cool down to 60° C.). Add oil heated to 60° C., homogenise at 350/100 bar, spray dry at 180/80° C. Ti/To. Processing steps (using heat processed and microfluidised Star Plus P) |
| Water | | 84.6% | Prepare 20% TS Star Plus P dispersion at 70° C., |
| Star Plus P | 37.5% | 5.8% | process in 73 × 82 mm cans at 121° C.-60 |
| Alanate 180 | 37.5% | 5.8% | minutes, cool down, add remaining water to |
| Tuna oil | 25.0% | 3.8% | make-up to 10% TS, microfluidise at 800 bar-3 |
| Total | 100.0% | 100.0% | passes. Prepare 15% TS NaCas solution at 60° C. and mix with processed starch above. |

| Ingredient | powder composition | emulsion composition |
|---|---|---|

(Preferably heat protein-starch mixture in cans at 98° C.-30 minutes, cool down to 60° C). Add oil heated to 60° C., homogenise at 350/100 bar, spray dry at 180/80° C. Ti/To.

Example 19

Formulations and Manufacture of Powders with 25% Tuna Oil (+Radiolabelled Tracer) in Heated Blends of Protein-Sugar-RS Starch as Encapsulants for in-vivo Testing

| Ingredient | Ingredient Wt. (g) | emulsion composition (%) | Processing steps (using heat processed and microfluidised Hylon VII starch) |
|---|---|---|---|
| Water | 82.47 | 82.04% | Prepare 20% TS starch dispersion at 70° C., process |
| Alanate 180 | 4.33 | 4.31% | in 73 × 82 mm cans at 121° C.-60 minutes, cool |
| Glucose | 4.33 | 4.31% | down, add remaining water to make-up to 10% TS, |
| Hylon VII | 4.33 | 4.31% | microfluidise at 800 bar-3 passes. Prepare 15% TS |
| Tuna oil | 4.56 | 4.54% | NaCas solution at 60° C., add sugar and mix with |
| Radiolabelled tracer [$^{14}$C] 18:3 | 0.50 ml (25 µCi) | 0.50% | processed starch above. (Preferably heat protein-glucose-starch mixture in cans at 98° C.-30 minutes, |
| Total solids | 18.05 | 18.0% | cool down to 60° C.). Add radiolabelled tuna oil, |
| Total | 100.52 | 100.0% | homogenise at 350/100 bars, spray dry at 180/80° C. Ti/To. |

Characteristics of Microcapsules In-Vitro

The properties of the example 1 formulations are shown in FIG. 1 of the drawings. Solvent-extractable fat in all powders (25% fat in powder) were less than 3% (of total fat) indicating that the encapsulating efficiency was good. Released oil in SGF was less than 2% of total fat for all formulations. Released oil in SGF+SIF were less than 4% of total fat for casein based microcapsules and up to 22% of total fat for WPI based microcapsules. In these examples NaCas based formulations offer better protection than WPI based formulations. Also heat treatment applied to WPI-sugar encapsulant can increase the release in SGF+SIF. Depending on the type of protein and whether heat treatment is applied to the encapsulant the core may be released targeted to a specific site in the GI tract.

Figure 2:
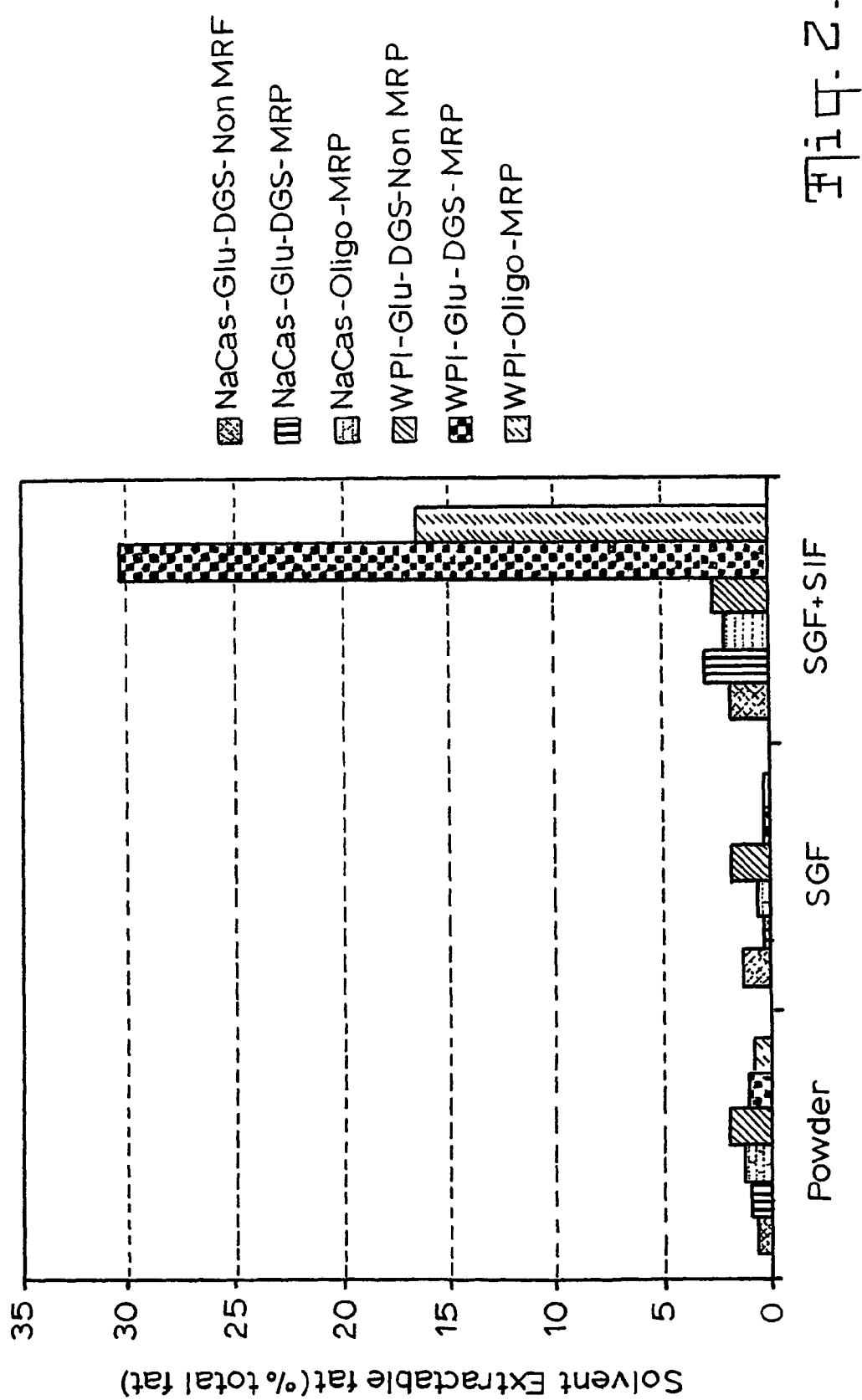
FIG. 2 shows the properties related to solvent extractable fat associated with formulations discussed in example 2.

The properties of the example 2 formulations are shown in FIG. 2 of the drawings. Solvent-extractable fat in all powders (50% fat in powder) were less than 3% (of total fat) indicating that the good encapsulating efficiency was maintained when that ratio of the fat to encapsulating material was increased from 1:3 in 25% fat powders to 1:1 in 50% fat powders. Released oil in SGF was less than 2% of total fat for all formulations. Released oil in SGF+SIF were less than 4% of total fat for casein based microcapsules and up to 30% of total fat for WPI based microcapsules. The trend in the release properties of the microcapsules in FIG. 2 with 50% fat powders mirror those observed in FIG. 1 for 25% fat powders. In these examples NaCas based formulations offer better protection than WPI based formulations. Also heat treatment applied to WPI-sugar encapsulant can increase the release in SGF+SIF. Depending on the type of protein and whether heat treatment is applied to the encapsulant the core may be released targeted to a specific site in the GI tract.

Figure 3:
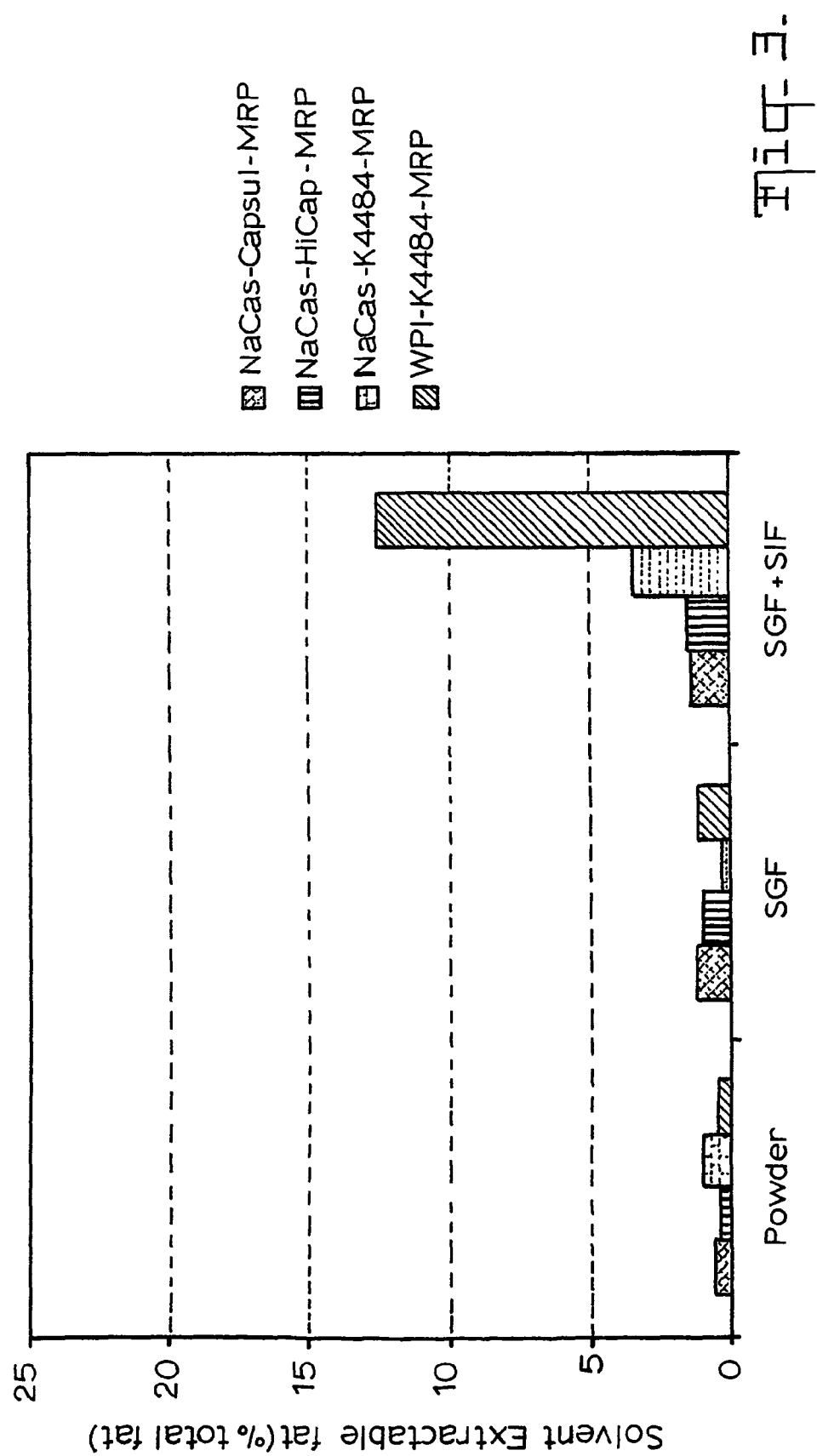
FIG. 3 shows the properties related to solvent extractable fat associated with formulations discussed in example 3.

The properties of the example 3 formulations are shown in FIG. 3 of the drawings. Formulations (25% fat powders) made with heated protein-starch as encapsulants had low solvent extractable fat (<1% of total fat). Released oil in SGF was less than 2% of total fat for all formulations. Released oil in SGF+SIF were less than 4% of total fat for casein based microcapsules and up to 12.5% of total fat for WPI based microcapsules. In these examples NaCas based formulations offers better protection than the WPI based formulation. Depending on the type of protein used the core may be released targeted to a specific site in the GI tract.

Figure 4:
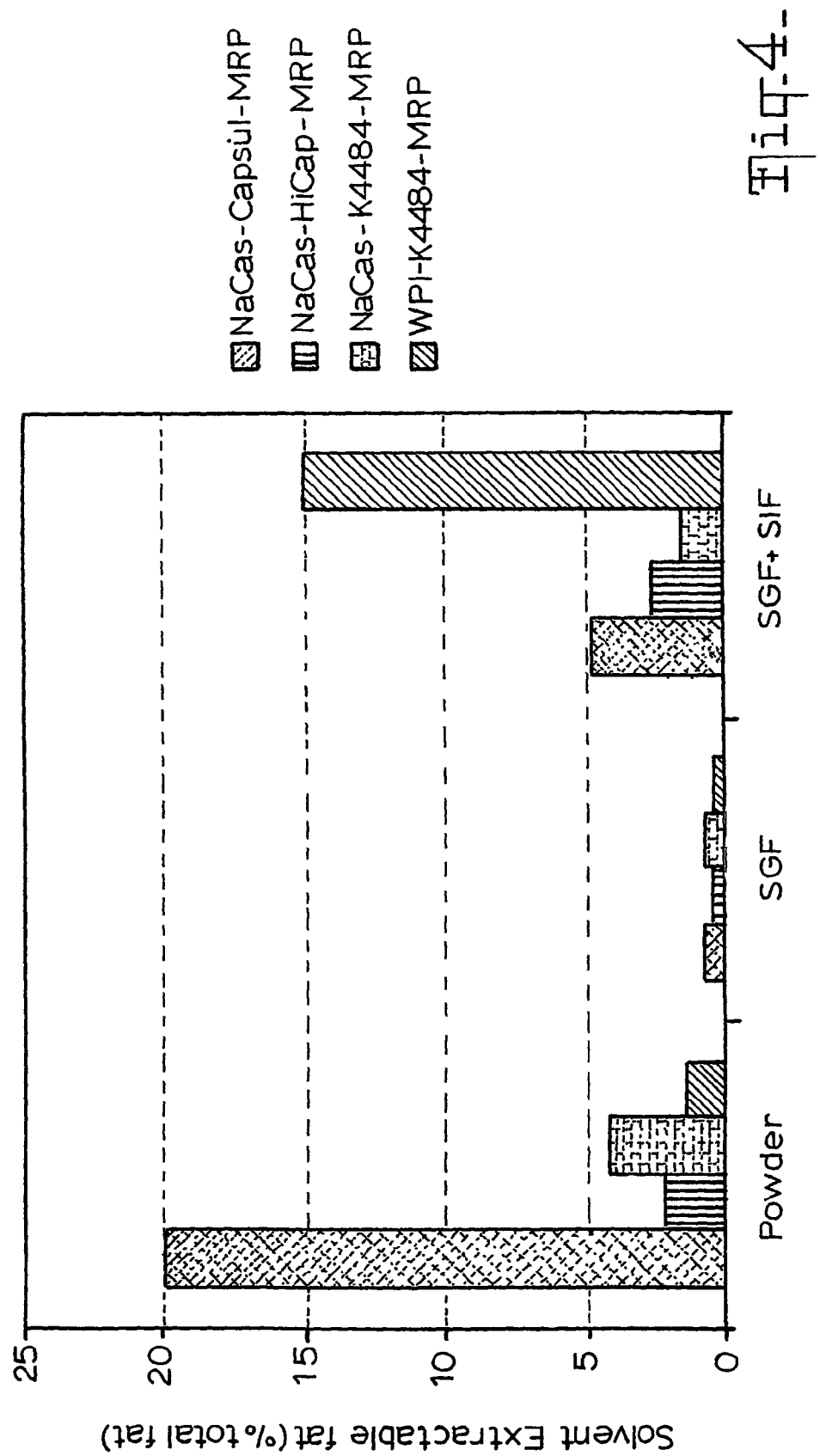
FIG. 4 shows the properties related to solvent extractable fat associated with formulations discussed in example 4.

The properties of the example 4 formulations are shown in FIG. 4 of the drawings. Formulations (50% fat powders) made with heated protein-starch as encapsulants had higher solvent extractable fat (1 to 20% of total fat) than corresponding formulation for 25% fat powders. Released oil in SGF was less than 2% of total fat for all formulations. Released oil in SGF+SIF were less than 5% of total fat for casein based microcapsules and up to 15% of total fat for WPI based microcapsules. In these examples NaCas based formulations offer better protection than the WPI based formulation. Depending on the type of protein used the core may be released targeted to a specific site in the GI tract. Solvent-extractable fat in powder was not related to solvent extractable fat in SGF and SIF fluids.

Figure 5:
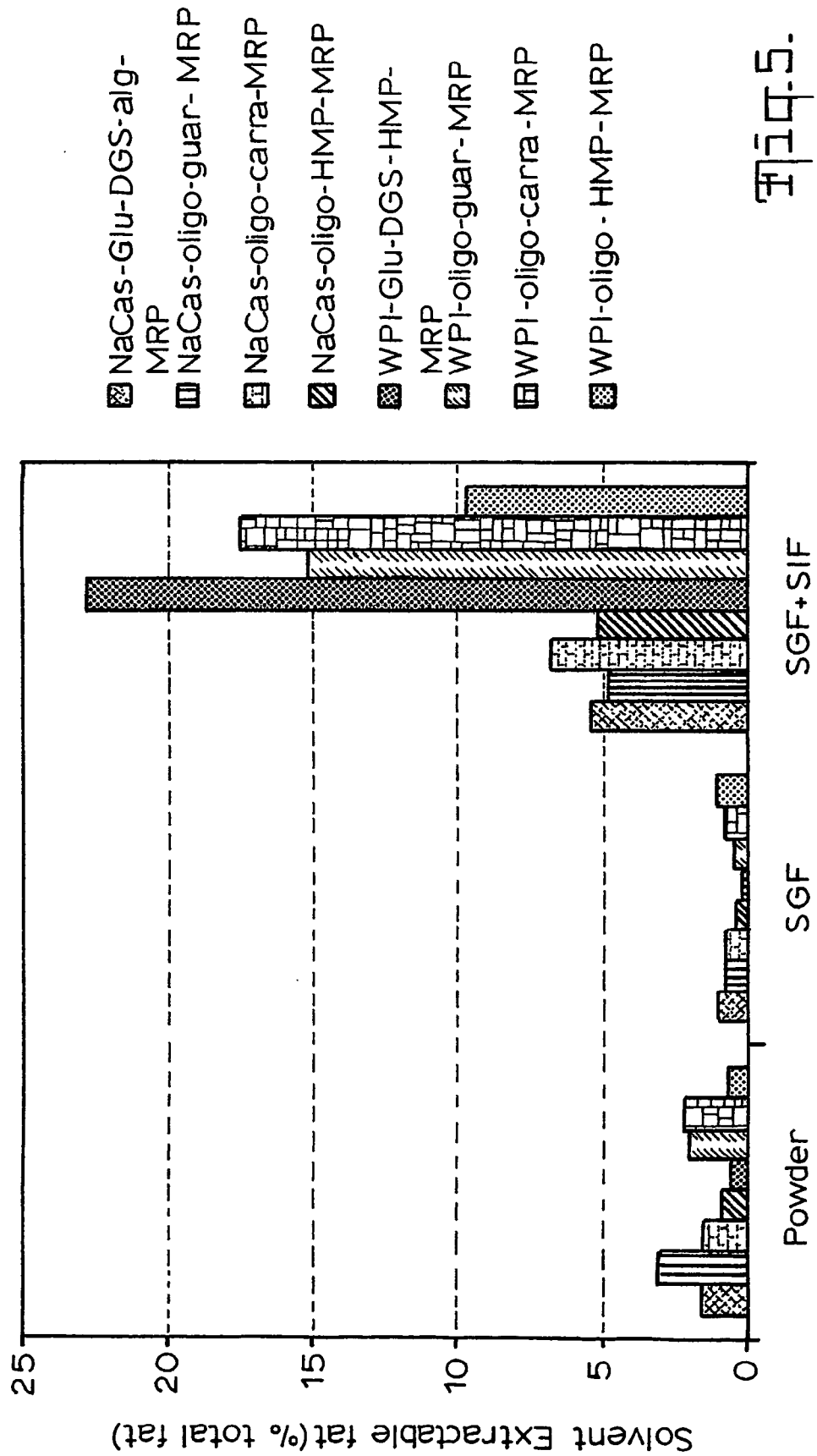
FIG. 5 shows the properties related to solvent extractable fat associated with formulations discussed in example 5.

The properties of the example 5 formulations are shown in FIG. 5 of the drawings. For 25% fat powders the use of gums in combination with protein-glucose/dried glucose syrup or protein-oligosaccharide as encapsulant resulted in powders with low extractable fat in powder (<3% of total fat) and in SGF (<2% of total fat). Released oil in SGF+SIF were less than 7% of total fat for casein based microcapsules and up to 22.8% of total fat for WPI based microcapsules. Caseinate-based formulations with gums released more fat (FIG. 5) than similar formulations without gum (FIG. 1) after sequential exposure to SGF and SIF. In these examples NaCas based formulations offer better protection than WPI based formulations. Depending on the type of protein used the core may be released targeted to a specific site in the GI tract.

Figure 6:
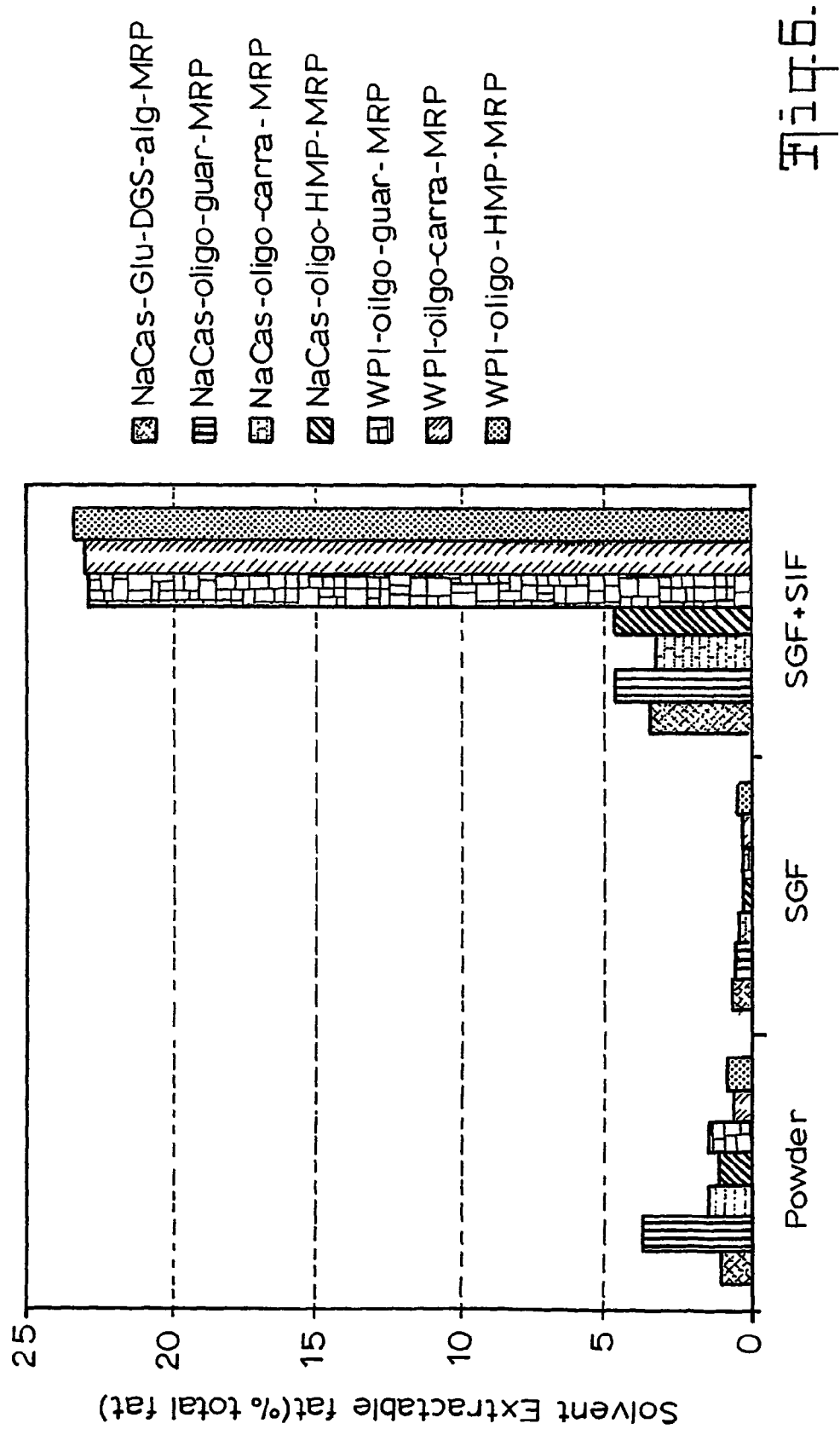
FIG. 6 shows the properties related to solvent extractable fat associated with formulations discussed in example 6.

The properties of the example 6 formulations are shown in FIG. 6 of the drawings. The trends observed for 50% fat powders containing gums in combination with protein-glucose/dried glucose syrup or oligosaccharide (FIG. 6) are similar to those observed for compositions with 25% fat powders (FIG. 5). All formulations had low extractable fat in powder (<4% of total fat) and SGF (<2% of total fat). Released oil in SGF+SIF were less than 5% of total fat for casein based microcapsules and up to 23% of total fat for WPI based microcapsules. The amount of oil released in 50% fat powders (FIG. 6) is significantly more than that in 25% fat powders (FIG. 5) after sequential exposure to SGF and SIF for WPI based formulations. In these examples NaCas based formulations offers better protection than WPI based formulations. Depending on the type of protein used the core may be released targeted to a specific site in the GI tract.

Figure 7:
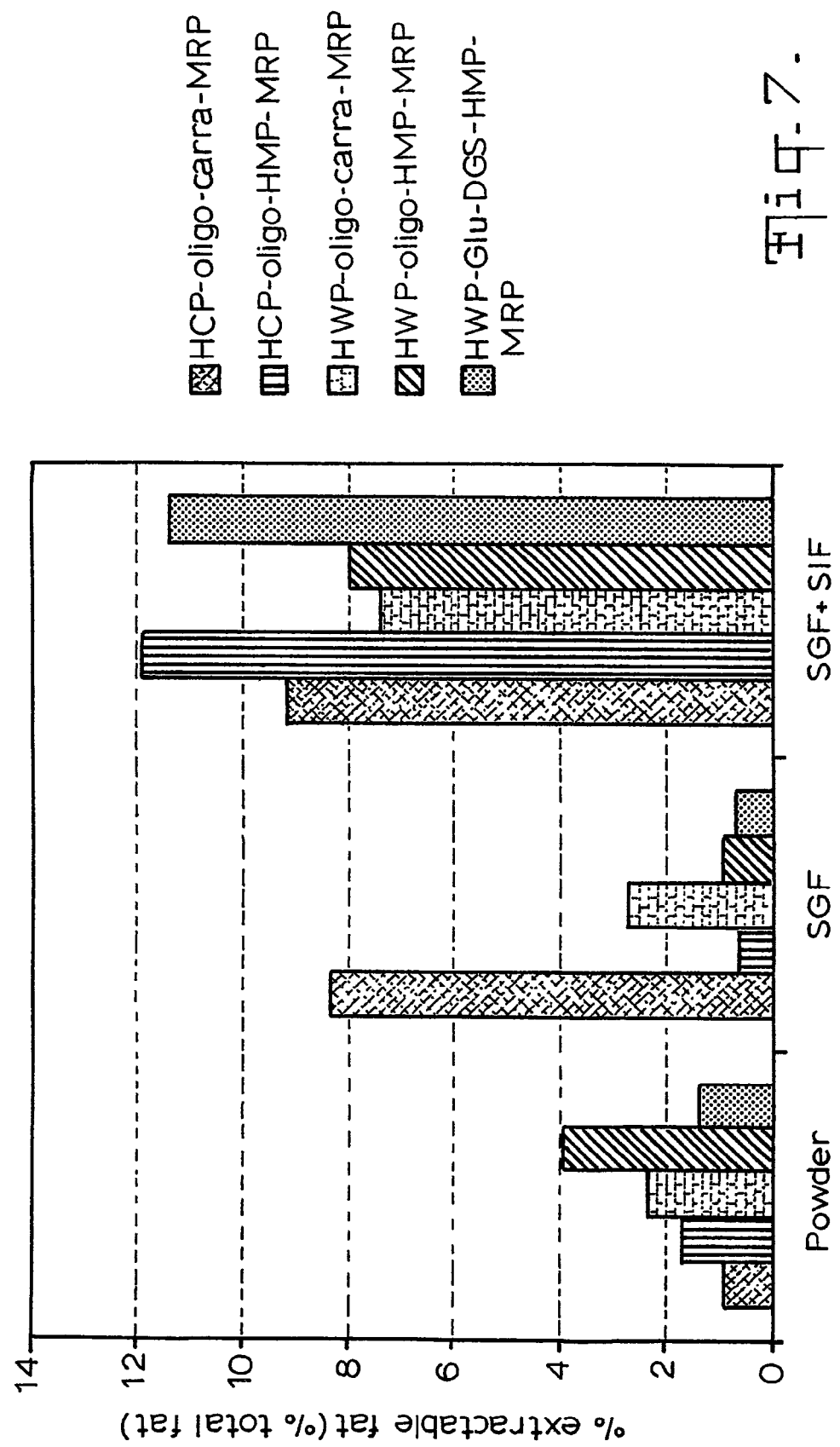
FIG. 7 shows the properties related to extractable fat associated with formulations discussed in example 7.

The properties of the example 7 formulations are shown in FIG. 7 of the drawings. Hydrolysed milk proteins can be used in place of whole proteins for encapsulation of oil. For 25% fat powders use of hydrolysed protein in combination with oligosaccharide and polysaccharide as encapsulant resulted in powders with low extractable fat in powder (<3% of total fat). Released oil in SGF was less than 9% of total fat for all formulations. Released oil in SGF+SIF was less than 12% in all formulations. While combinations of hydrolysed casein with oligosaccharide and polysaccharides were less effective for protecting oils from release in SGF+SIF compared to corresponding formulations with the parent protein (Na caseinate), the reverse trend was found with the use of hydrolysed whey protein with oligosaccharide and carrageenan (Compare FIGS. 5 and 7).

Figure 8:
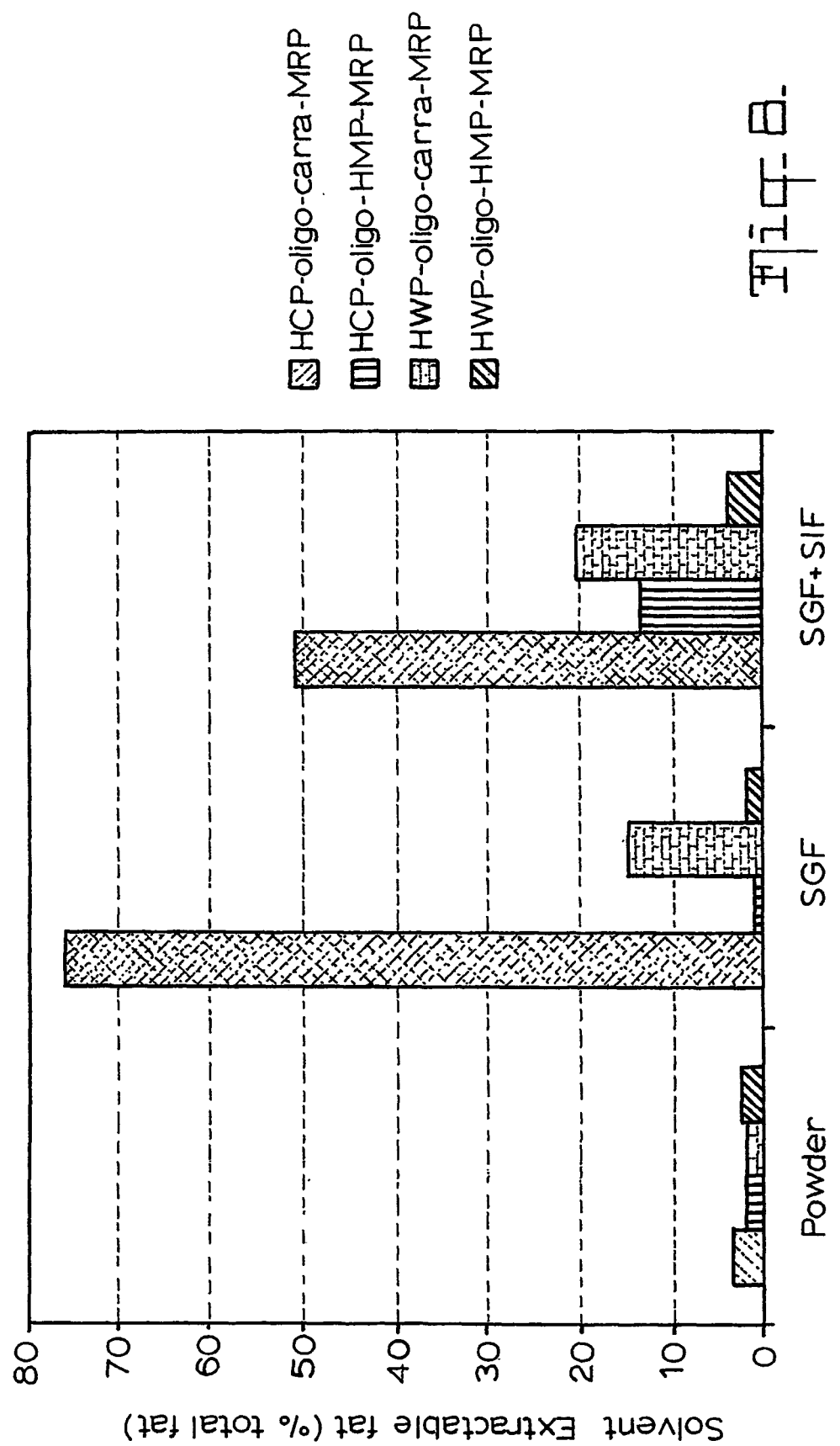
FIG. 8 shows the properties related to solvent extractable fat associated with formulations discussed in example 8.

The properties of the example 8 formulations are shown in FIG. 8 of the drawings. For 50% fat powders use of hydrolysed protein in combination with oligosaccharide and polysaccharide as encapsulant resulted in powders with low extractable fat in powder (<3% of total fat). While solvent-extractable fat in powders (50% fat) was low, the hydrolysed casein-based formulation containing carrageenan released a significant amount of the oil in SGF (77% of total fat) and in SGF+SIF (51% of total fat). This formulation will be a suitable delivery system if the site for target delivery is the stomach or small intestine. Those containing hydrolysed casein or hydrolysed whey protein with high methoxy pectin were comparatively better at protecting their load than those with carrageenan with release in SGF+SIF less than 3% of total fat. In these examples HWP based formulation offers better protection than HCP based formulation. Depending on the type of protein-polysaccharide combination used the core may be released targeted to a specific site in the GI tract.

Figure 9:
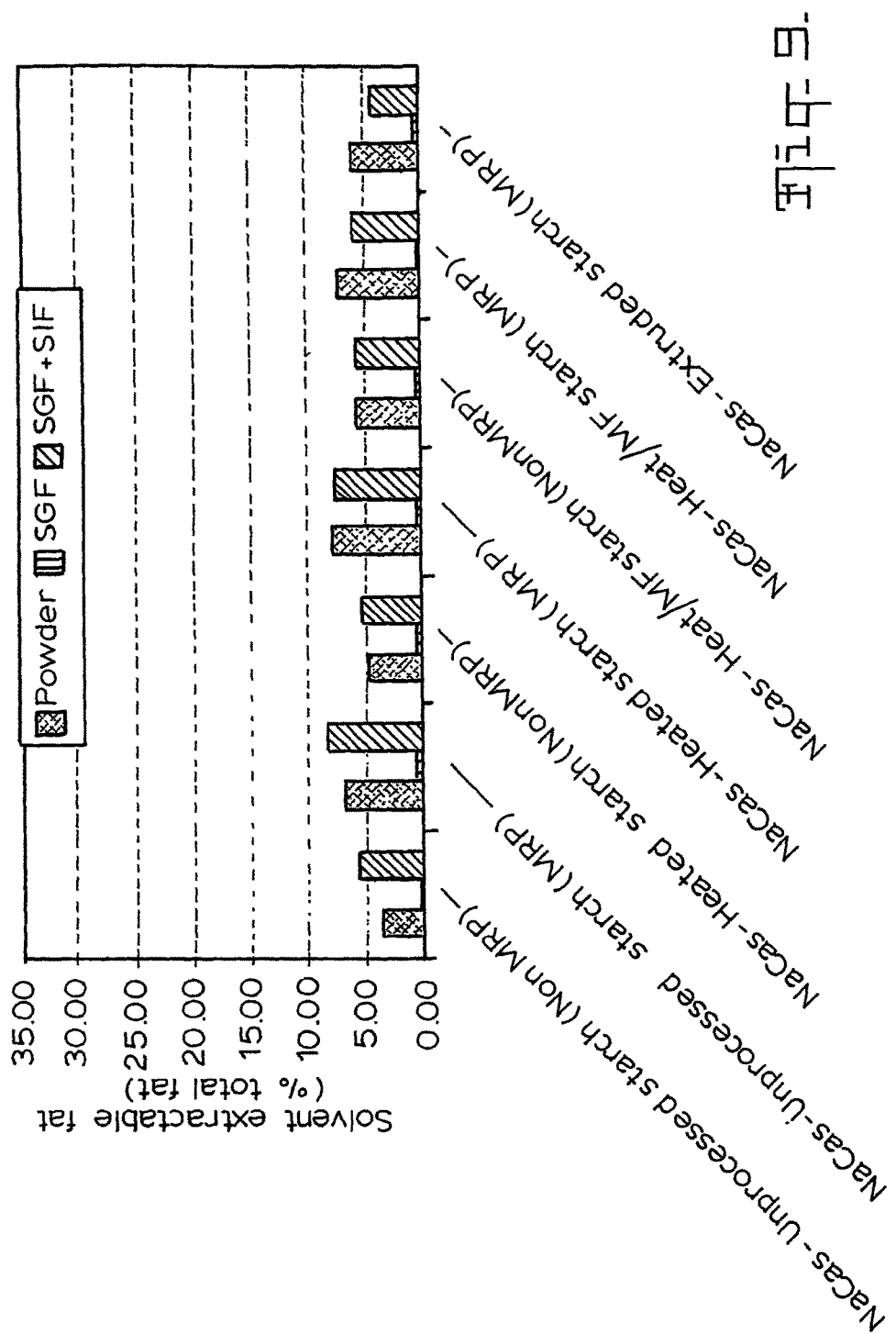
FIG. 9 shows the properties related to solvent extractable fat associated with formulations discussed in example 9.

The properties of the example 9 formulations are shown in FIG. 9 of the drawings. The results show that 25% fat powders made with unheated and heated combinations of caseinate and raw or pre-processed potato starch had solvent-extractable fat of between 3-8% of total fat, which was generally higher than those made with combinations of proteins with sugar/dried glucose syrup or oligosaccharides. All formulations with potato starch have very low oil release in-vitro. Exposure to SGF resulted in release of <0.6% of total fat and sequential exposure to SGF and SIF resulted in between 4-8% of total fat being released.

Figure 10:
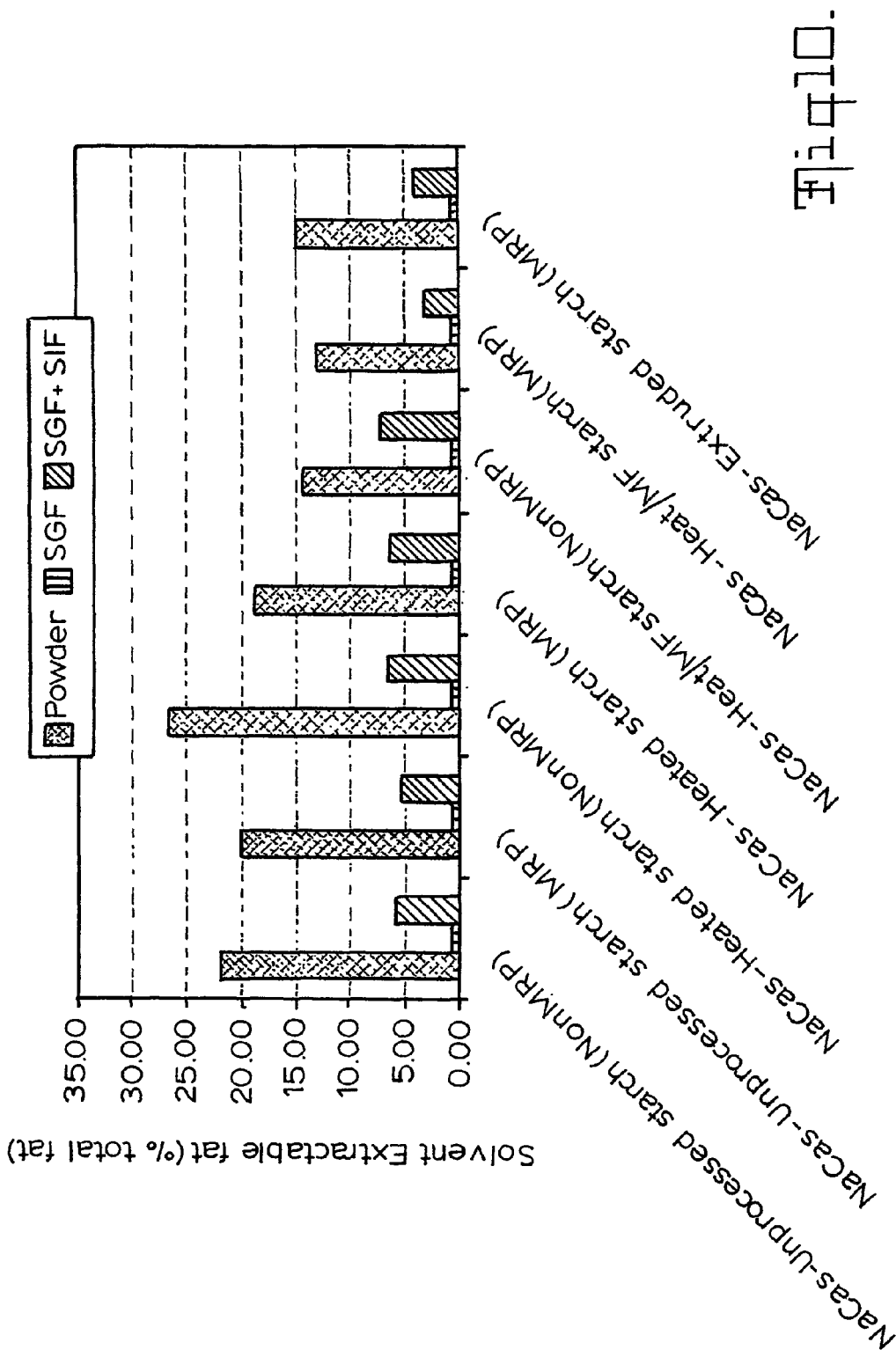
FIG. 10 shows the properties related to solvent extractable fat associated with formulations discussed in example 10.

The properties of the example 10 formulations are shown in FIG. 10 of the drawings. The results show that 25% fat powders made with unheated and heated combinations of caseinate and unprocessed or pre-processed Hylon VII had solvent-extractable fat of between 13-26% of total fat, which was generally higher than those made with combinations of proteins with sugar/dried glucose syrup or oligosaccharides or potato starch indicating that encapsulation efficiencies of formulations with Hylon VII were significantly lower. Use of Hylon VII that had been subjected to microfluidisation or extrusion prior to combination with protein improved encapsulation efficiency. All formulations with Hylon VII have very low oil release in-vitro. Exposure to SGF which results in hydration of the capsule resulted in minimal release of <0.8% of total fat and sequential exposure to SGF and SIF resulted in between 3-7% of total fat being released.

Figure 11:
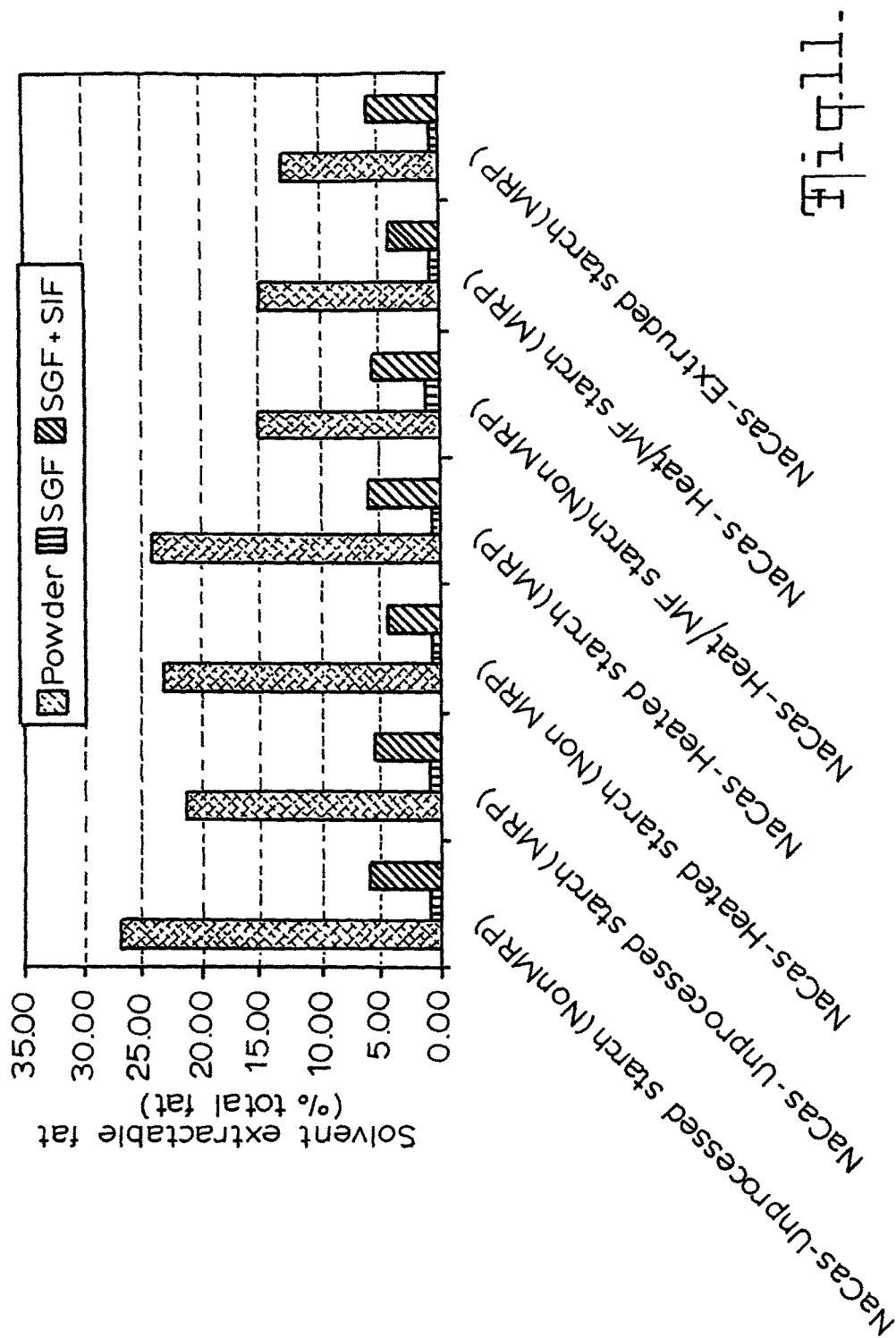
FIG. 11 shows the properties related to solvent extractable fat associated with formulations discussed in example 11.

The properties of the example 11 formulations are shown in FIG. 11 of the drawings. The results show that 25% fat powders made with unheated and heated combinations of caseinate and unprocessed or pre-processed Hi-Maize had solvent-extractable fat of between 13-26% of total fat. Use of Hi-Maize that had been subjected to microfluidisation or extrusion prior to combination with protein improved encapsulation efficiency. All formulations with Hi-Maize have very low oil release in-vitro. Exposure to SGF which results in hydration of the capsule resulted in minimal release of <1% of total fat and sequential exposure to SGF and SIF resulted in between 4-6% of total fat being released.

Figure 12:
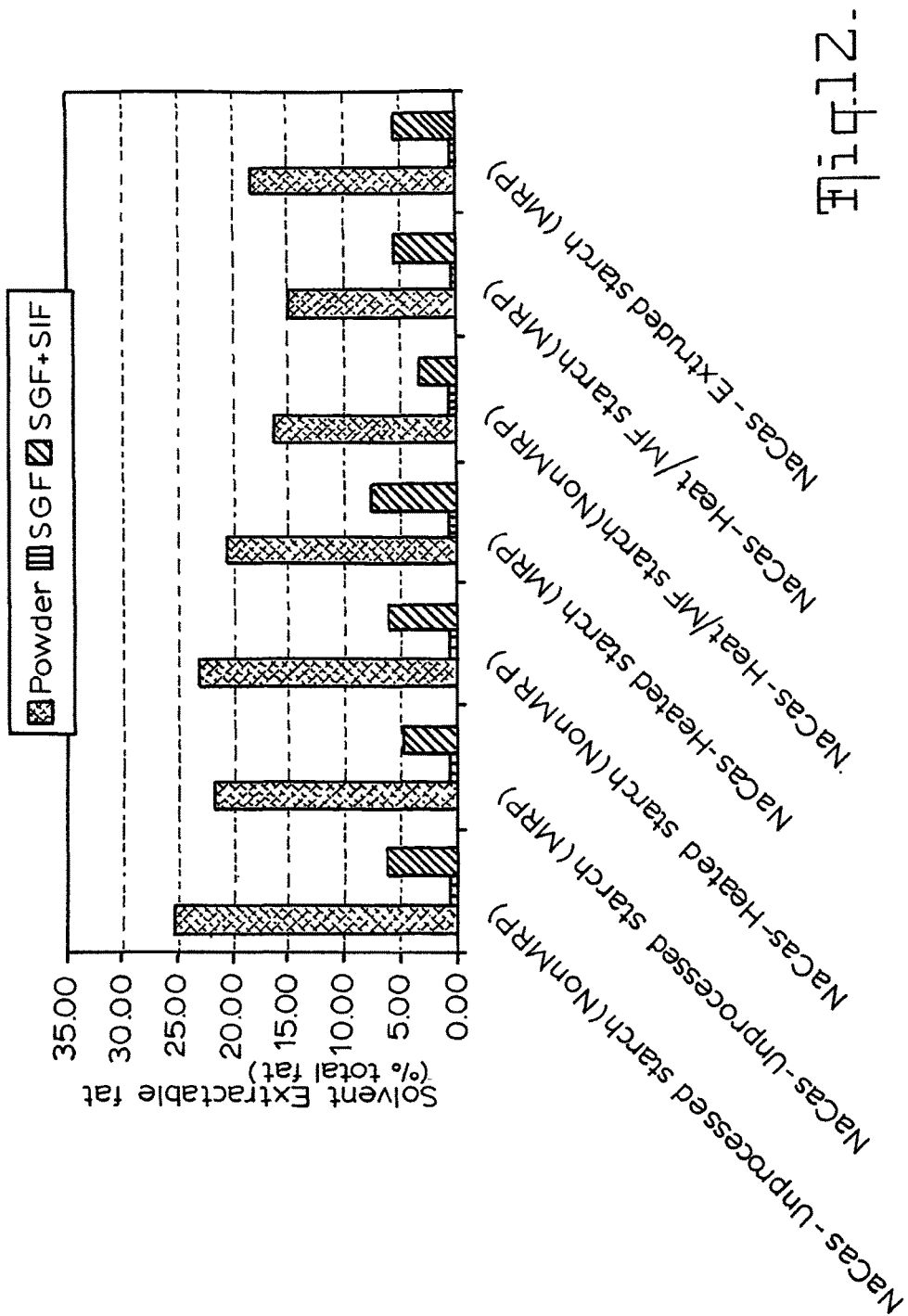
FIG. 12 shows the properties related to solvent extractable fat associated with formulations discussed in example 12.

The properties of the example 12 formulations are shown in FIG. 12 of the drawings. The results show that 25% fat powders made with unheated and heated combinations of caseinate and unprocessed or pre-processed Novelose 260 had solvent-extractable fat of between 14-25% of total fat. Use of Novelose 260 that had been subjected to microfluidisation prior to combination with protein improved encapsulation efficiency. All formulations with Novelose 260 have very low oil release in-vitro. Exposure to SGF which results in hydration of the capsule resulted in minimal release of <1% of total fat and sequential exposure to SGF and SIF resulted in between 2-6% of total fat being released. The characteristics of formulations with Novelose 260 were similar to those observed for formulations with Hylon VII (FIG. 10) or Hi-Maize (FIG. 11), which like Novelose 260 (FIG. 12) are RS2 type starches.

Figure 13:
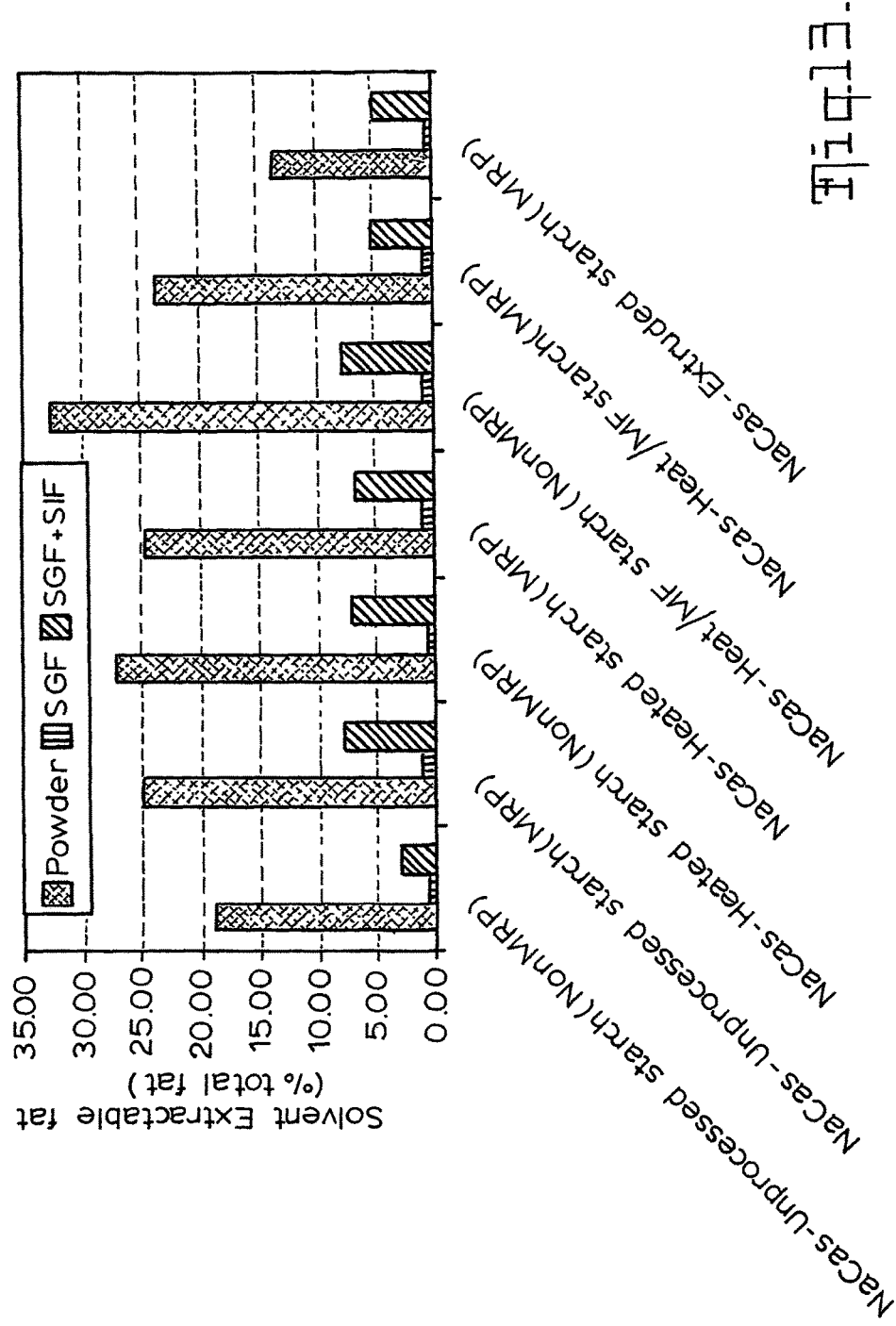
FIG. 13 shows the properties related to solvent extractable fat associated with formulations discussed in example 13.

The properties of the example 13 formulations are shown in FIG. 13 of the drawings. The results show that 25% fat powders made with unheated and heated combinations of caseinate and unprocessed or pre-processed Novelose 330 (an RS3 type starch) had solvent-extractable fat of between 13-33% of total fat. Use of Novelose 330 that had been subjected to extrusion prior to combination with protein improved encapsulation efficiency. All formulations with Novelose 330 have very low oil release in-vitro. Exposure to SGF which results in hydration of the capsule resulted in minimal release of <1% of total fat and sequential exposure to SGF and SIF resulted in between 3.1-8.0% of total fat being released.

Figure 14:
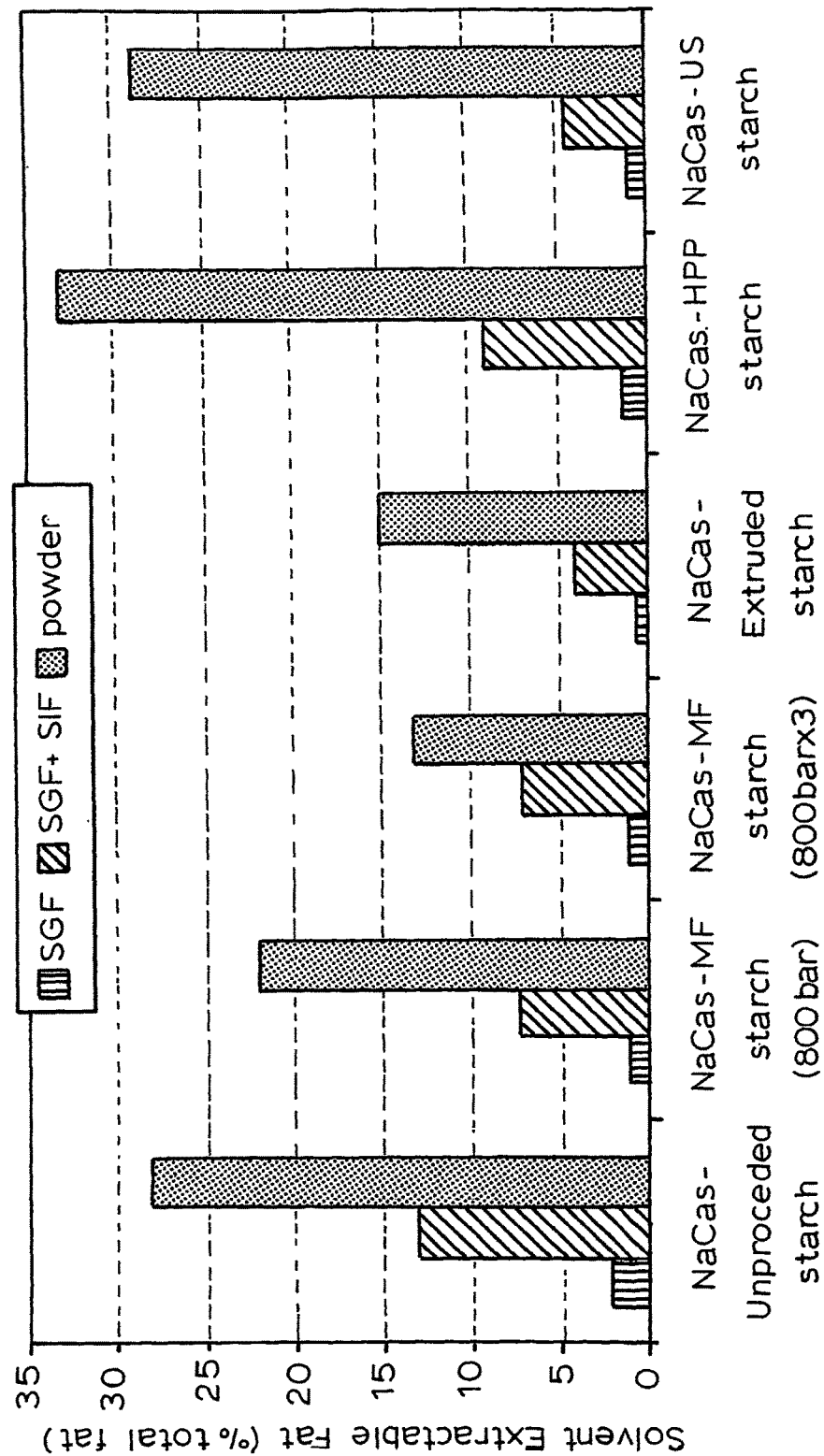
FIG. 14 shows the properties related to solvent extractable fat associated with formulations discussed in example 14.

The properties of the example 14 formulations are shown in FIG. 14 of the drawings. The results demonstrate that pre-processing of starches using emerging food processing technologies (i.e. microfluidisation, high pressure processing or ultrasonication) and extrusion could improve the properties of starches used in combination with casein as delivery systems to the GI tract. Released oil in SGF was less than 1.2% of total fat for pre-processed starches. Released oil in SGF+SIF was less than 10% in pre-processed starches. All pre-processed starches have lower oil released in-vitro compared to the formulation containing unprocessed starch.

Figure 15:
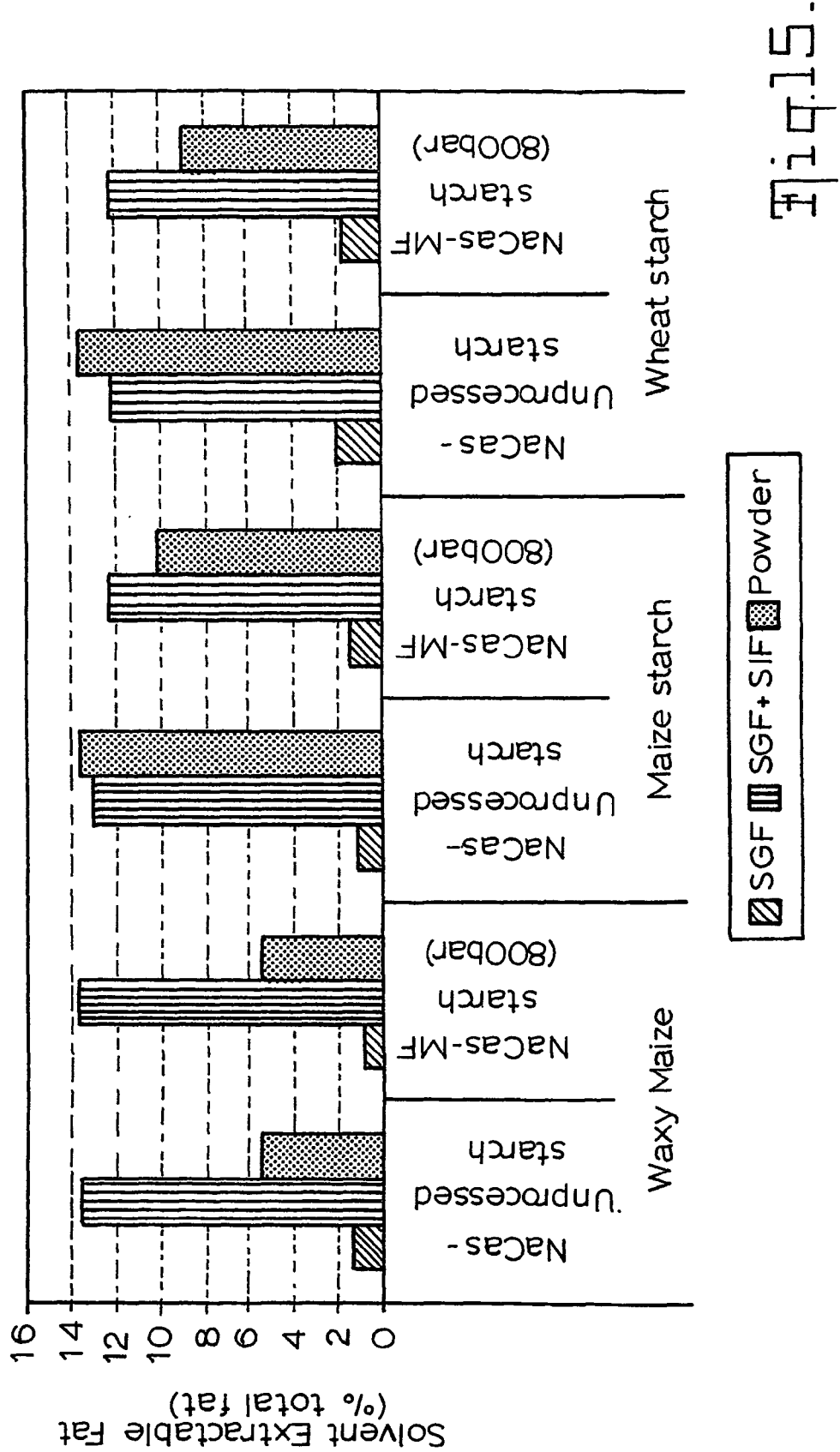
FIG. 15 shows the properties related to solvent extractable fat associated with formulations discussed in example 15.

The properties of the example 15 formulations are shown in FIG. 15 of the drawings. The results demonstrate that use of native non-RS starch and their pre-processed counterparts in combination with protein produced powders with solvent extractable fat of between 5.5-13.6% of total fat. Released oil in SGF was less than 2% of total fat. Released oil in SGF+SIF was between 12-14% (FIG. 15), which was slightly higher than that observed when resistant starches were used in combination with protein for microencapsulation (See FIGS. 9-14).

Figure 16:
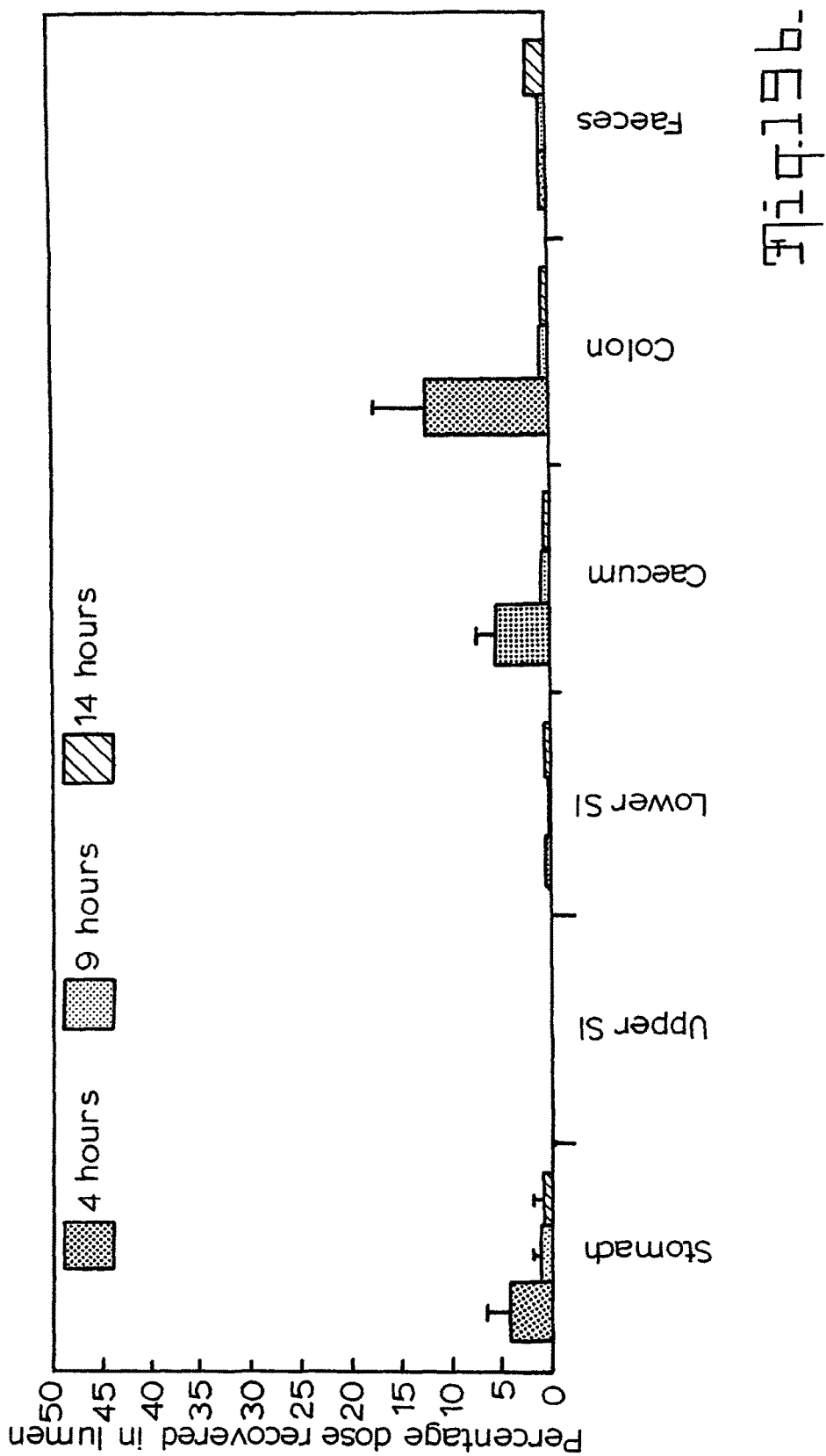
FIG. 16 shows the properties of example 16 formulations containing lutein-in-oil.

The properties of the example 16 formulations containing lutein-in-oil are shown in FIG. 16 of the drawings. The results demonstrate that lutein was protected in the powder microcapsule (0.4-2.5% unencapsulated lutein). Released lutein in SGF was also very low (2.5-4% of total lutein). Released lutein in SGF+SIF was between 34-51% (FIG. 16).

Figure 17:
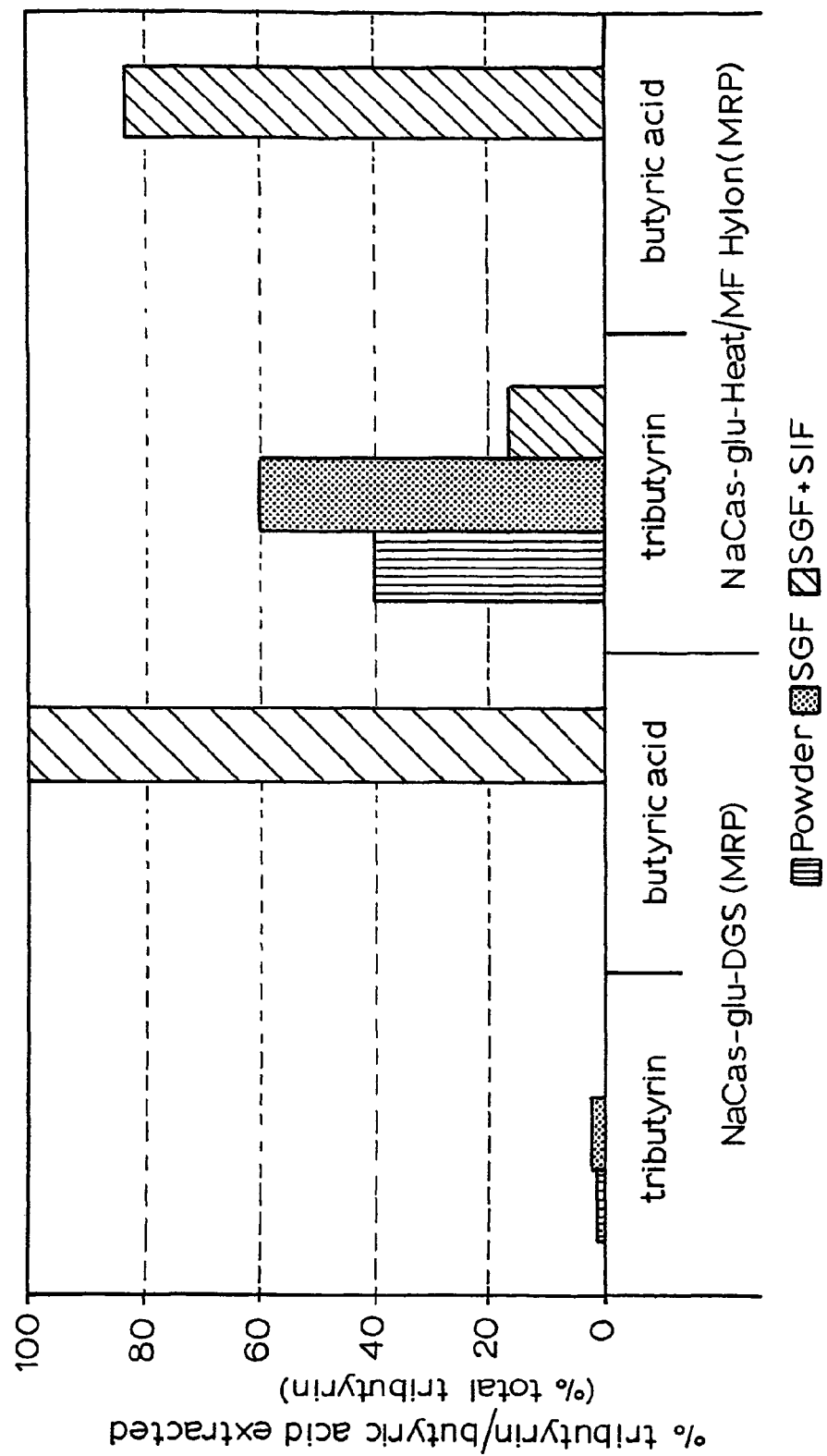
FIG. 17 shows the properties of example 17 formulations containing tributyrin.

The properties of the example 17 formulations containing tributyrin are shown in FIG. 17 of the drawings. All the tributyrin was released after sequential exposure to SGF and SIF in NaCas-sugar formulation, and up to 83% in NaCas-sugar-RS starch formulation. These results suggest that formulation with RS starch has improved the protection of tributyrin in the GI tract.

Figure 18:
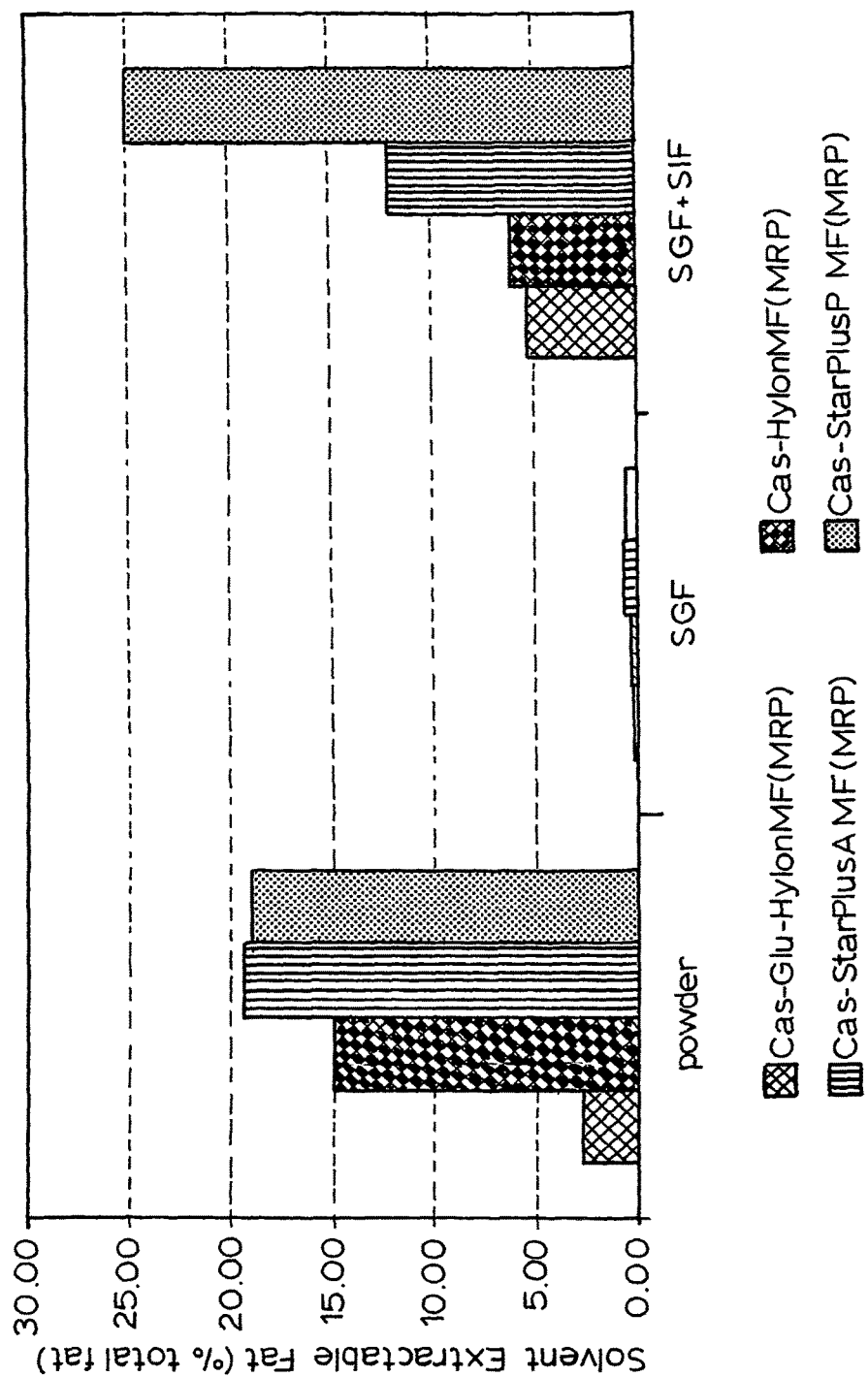
FIG. 18 shows the properties of example 18 formulations containing 25% tuna oil in heated blends of NaCas-sugar-HylonMF, NaCas-HylonMF, or NaCas-StarPlus MF as encapsulants.

The properties of the example 18 formulations containing 25% tuna oil in heated blends of NaCas-sugar-HylonMF or NaCas-HylonMF or NaCas-StarPlus MF as encapsulants are shown in FIG. 18 of the drawings. The results demonstrate that addition of Glucose into an NaCas-Hylon formulation can improve the encapsulation efficiency of the powder microcapsule without affecting the release in SGF and SGF+SIF. Use of acetylated starch (StarPlus A) or proprionylated starch (Starplus P) in place of Hylon in formulations containing resistant starch in combination with NaCas increased the release in SGF+SIF from 5% for Hylon to 12% and 25% for Star Plus A and StarPlus P respectively (FIG. 18), but there was no difference in the amount of release in SGF.

Release Characteristics of Tuna Oil Microcapsules In-Vivo

Figure 19A:
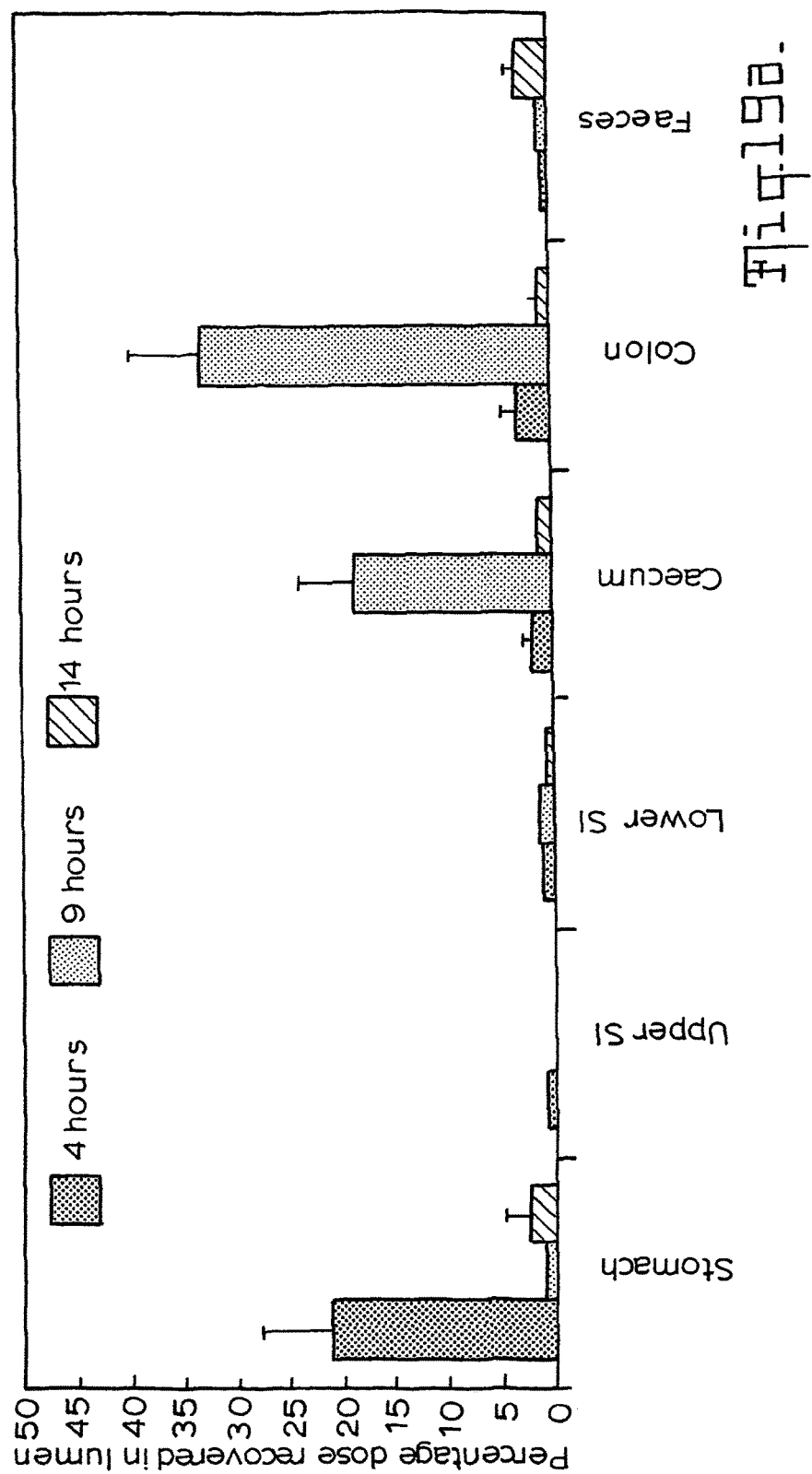

The result of the in-vivo experiment (example 19 formulation) is shown in FIGS. 19a and 19b of the drawings. Lumen contents were expressed as a percentage of dose of radioactivity given to indicate relative abundance between the treatment groups. The figures show the percentage of administered dose of radioactivity recovered after dosing with C14 trilinolenein as free oil after 4, 9, and 14 hours. This includes lumen contents, tissue and faeces. Data is expressed as percentage of total lumen radioactivity to show relative distribution across the system. All rats n=5 in each case except for FIG. 19b at 14 hours where n=4.

The results indicated that the treatment with microencapsulated oil at 9 hours resulted in greater caecum and colon (18% and 35%) radioactivity (FIG. 19a) than treatment with free oil, where only about 5% in caecum at 4 hours and about 10% in colon at 4 hours, with minimal amounts of radioactivity at 9 hours (FIG. 19b). Radioactivity levels in the lumen for the treatment with free oil were low at all time points, which indicates that even by 4 hours there may be significant uptake and metabolism to $CO_2$. Overall the in-vivo study indicates that the process of microencapsulation was reasonably successful in protecting the fish oil against early uptake and metabolism in the stomach and upper GI tract. For the treatment with microencapsulated oils the recovery was high at 4 and 9 hours, and at these time points the radioactivity was either in the stomach at 4 hours or caecum and colon at 9 hours. High amounts in the caecum and colon indicates that the microencapsulated oil passed the small intestine without significant absorption. For the free oil, smaller amounts reached the caecum and colon, primarily because the recovery of the given dose was low at all time points indicating greater metabolism. Even at 4 hour time point the oil had already transited the small intestine. There was little radiolabel retained in the tissues at 14 hour in either group, which indicates that conversion to endogenous lipids was not significant.

From the above those skilled in the art will see that the present invention provides a simple to use yet effective delivery vehicle to the colon as well as preserving sensitive core ingredients during storage and processing. Those skilled in the art will also realise that this invention can be implemented in a number of different embodiments by varying the encapsulant proteins and carbohydrates without departing from the teachings of this invention.

The invention claimed is:

1. An encapsulated therapeutic or nutritional agent that is the product of a process comprising the steps of:
    (A) treating a water-insoluble resistant starch to increase the number of sugar reducing groups in the resulting treated starch, wherein the treating is selected from the group consisting of heating, extrusion, high pressure processing, microfluidisation, and ultrasonication;
    (B) forming a dispersion of a film-forming protein and the treated starch in an aqueous phase, wherein the dispersion has a protein:starch ratio of from about 1:1 to about 1:2;
    (C) heating the dispersion to induce formation of Maillard reaction products;
    (D) mixing a storage-unstable therapeutic or nutritional agent with the dispersion to form a mixture; and then
    (E) homogenizing the mixture to obtain an agent-in-water emulsion,
    wherein the treated starch and the film-forming protein encapsulate the agent with a protective shell, which shell allows release of the agent in the gastrointestinal tract.

2. The encapsulated therapeutic or nutritional agent of claim 1, wherein the process further comprises spray drying the emulsion.

3. The encapsulated therapeutic or nutritional agent of claim 1, wherein the film-forming protein includes milk proteins.

4. The encapsulated therapeutic or nutritional agent of claim 1, wherein the agent comprises at least one agent selected from the group consisting of lipids, oil soluble, and oil dispersible ingredients.

5. The encapsulated therapeutic or nutritional agent of claim 1, wherein the starch comprises wheat starch.

6. The encapsulated therapeutic or nutritional agent of claim 1, wherein step (A) comprises microfluidisation.

7. The encapsulated therapeutic or nutritional agent of claim 1, wherein step (A) comprises ultrasonication.

8. The encapsulated therapeutic or nutritional agent of claim 1, wherein step (A) comprises treating the starch with high pressure processing.

9. The encapsulated therapeutic or nutritional agent of claim 1, wherein the agent-in-water emulsion is comprised of at least 60% water.

10. An encapsulated therapeutic or nutritional agent that is the product of a process comprising the steps of:
    (A) treating a water-insoluble resistant starch to increase the number of sugar reducing groups in the resulting treated starch, wherein the treating is selected from the group consisting of heating, extrusion, high pressure processing, microfluidisation, and ultrasonication;
    (B) forming a dispersion of a film-forming protein and the treated starch in an aqueous phase;
    (C) heating the dispersion to induce formation of Maillard reaction products;

(D) mixing a storage-unstable therapeutic or nutritional agent with the dispersion to form a mixture; and then (E) homogenizing the mixture to obtain an agent-in-water emulsion that is comprised of at least 60% water, wherein the treated starch and the film-forming protein encapsulate the agent with a protective shell, which shell allows release of the agent in the gastrointestinal tract.

11. The method of claim 1, wherein the water-insoluble resistant starch is an RS2 or RS3 starch.

* * * * *